US010822357B2

(12) United States Patent
Yano et al.

(10) Patent No.: US 10,822,357 B2
(45) Date of Patent: Nov. 3, 2020

(54) BENZYL COMPOUND

(71) Applicant: SEKISUI MEDICAL CO., LTD., Chuo-ku (JP)

(72) Inventors: Shinya Yano, Iwate (JP); Yuki Wakasugi, Iwate (JP); Yosuke Iwanaga, Iwate (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 0 days.

(21) Appl. No.: 15/755,705

(22) PCT Filed: Aug. 25, 2016

(86) PCT No.: PCT/JP2016/074888
§ 371 (c)(1),
(2) Date: Feb. 27, 2018

(87) PCT Pub. No.: WO2017/038650
PCT Pub. Date: Mar. 9, 2017

(65) Prior Publication Data
US 2019/0023726 A1    Jan. 24, 2019

(30) Foreign Application Priority Data

Aug. 28, 2015 (JP) ................................. 2015-168711
Nov. 20, 2015 (JP) ................................. 2015-227234
Jun. 23, 2016 (JP) ................................. 2016-124192

(51) Int. Cl.
*C07F 7/18* (2006.01)
*C07B 51/00* (2006.01)
*C07K 1/06* (2006.01)

(52) U.S. Cl.
CPC ............ *C07F 7/1892* (2013.01); *C07B 51/00* (2013.01); *C07F 7/1804* (2013.01); *C07K 1/062* (2013.01);
(Continued)

(58) Field of Classification Search
None
See application file for complete search history.

(56) References Cited

U.S. PATENT DOCUMENTS 4,695,643 A    9/1987 Oertle et al.
4,801,719 A    1/1989 Oertle et al.
(Continued)

FOREIGN PATENT DOCUMENTS

CN    101555232 A    10/2009
JP    52-102229    8/1977
(Continued)

OTHER PUBLICATIONS

Extended European Search Report dated Mar. 28, 2019 in the corresponding European Application No. 16841682.4 10 pages.
(Continued)

*Primary Examiner* — Clinton A Brooks
(74) *Attorney, Agent, or Firm* — Oblon, McClelland, Maier & Neustadt, L.L.P.

(57) ABSTRACT

The purpose of the present invention is to provide a protecting group which improves the solubility of a compound having a functional group protected with the protecting group in an organic solvent and which is easily separated and purified after a reaction with avoiding solidification or insolubilization. Provided is a benzyl compound represented by Formula (1) where $X^1$ represents —$CH_2OR^{14}$ (where $R^{14}$ represents a hydrogen atom, a halogenocarbonyl group, or an active ester-type protecting group), —$CH_2NHR^{15}$ (where $R^{15}$ represents a hydrogen atom, a linear or branched alkyl group having 1 to 6 carbon atoms, or an aralkyl group), a halogenomethyl group, a methyl azide group, a formyl group, or an oxime; and at least one of $R^1$, $R^2$, $R^3$, $R^4$, and $R^5$ is a group represented by Formula (2), and the remainders each represent a hydrogen atom, a halogen atom, an alkyl group having 1 to 4 carbon atoms, or an alkoxy group having
(Continued)

1 to 4 carbon atoms, where $R^6$ represents a linear or branched alkylene group having 1 to 16 carbon atoms; $X^2$ represents O or $CONR^{16}$ (where $R^{16}$ represents a hydrogen atom or an alkyl group having 1 to 4 carbon atoms); and A represents a group represented by Formula (3), (4), (5), (6), (7), (8), (9), (10), (11), (12), or (13).

13 Claims, 1 Drawing Sheet

(52) U.S. Cl.
    CPC .............. *C07K 1/063* (2013.01); *C07K 1/065* (2013.01); *Y02P 20/55* (2015.11)

(56) References Cited

U.S. PATENT DOCUMENTS

| | | | |
|---|---|---|---|
| 2002/0037895 A1 | 3/2002 | Baenteli et al. |
| 2003/0087903 A1 | 5/2003 | Baenteli et al. |
| 2005/0013843 A1 | 1/2005 | Detty et al. |
| 2005/0038016 A1 | 2/2005 | Connolly et al. |
| 2007/0037846 A1 | 2/2007 | Fretz et al. |
| 2007/0265446 A1 | 11/2007 | Connolly et al. |
| 2008/0009486 A1 | 1/2008 | Chen et al. |
| 2008/0026027 A1 | 1/2008 | Detty et al. |
| 2010/0130514 A1 | 5/2010 | Miyagi et al. |
| 2011/0196770 A1 | 8/2011 | Orr |
| 2012/0059149 A1 | 3/2012 | Takahashi |
| 2013/0210795 A1 | 8/2013 | Vakalopoulos et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2013/0303505 A1 | 11/2013 | Bollu et al. |
| 2014/0005359 A1 | 1/2014 | Takahashi |
| 2014/0303232 A1 | 10/2014 | Baryza et al. |
| 2015/0018343 A1 | 1/2015 | Swinnen et al. |
| 2015/0099770 A1 | 4/2015 | Hori et al. |
| 2015/0196672 A1 | 7/2015 | Cesati et al. |
| 2016/0106842 A1 | 4/2016 | Baryza et al. |
| 2016/0130230 A1 | 5/2016 | Vakalopoulos et al. |

FOREIGN PATENT DOCUMENTS

| | | |
|---|---|---|
| JP | 61-91193 | 5/1986 |
| JP | 2000-290285 A | 10/2000 |
| JP | 2002-533299 A | 10/2002 |
| WO | 93/06118 A1 | 4/1993 |
| WO | 00/18790 | 4/2000 |
| WO | 00/48989 A1 | 8/2000 |
| WO | 2004/063292 A2 | 7/2004 |
| WO | 2005/000281 A2 | 1/2005 |
| WO | 2005/005395 A2 | 1/2005 |
| WO | WO 2007/009250 A1 | 1/2007 |
| WO | 2008/133128 A1 | 11/2008 |
| WO | 2011/071565 A1 | 6/2011 |
| WO | 2012/000945 A1 | 1/2012 |
| WO | 2012/029794 A1 | 3/2012 |
| WO | 2013/091773 A1 | 6/2013 |
| WO | 2013/156869 A1 | 10/2013 |
| WO | 2013/175281 A1 | 11/2013 |
| WO | 2013/186612 A1 | 12/2013 |
| WO | 2014/026079 A2 | 2/2014 |
| WO | 2014/136086 A1 | 9/2014 |
| WO | 2014/175330 A1 | 10/2014 |
| WO | 2015/144799 A1 | 10/2015 |
| WO | 2016/037053 A1 | 3/2016 |
| WO | 2016/110237 A1 | 7/2016 |

OTHER PUBLICATIONS

Sebastiano Guerra, et al., "A quantitative assessment of chemical perturbations in thermotropic cyanobiphenyls", Physical Chemistry Chemical Physics, vol. 18, No. 21, May 13, 2016, pp. 14479-14494.
Yasuyuki Yamada, et al., "Supplementary Information for Repetitive Stepwise Rotaxane Formation toward Programmable Molecular Arraying", Chemical Communications, Jan. 1, 2013, pp. 1-34, Retrieved from the Internet: URL: http://www.rsc.org/suppdata/cc/c3/c3cc46859c/c3cc46859c.pdf.
Office Action dated Feb. 6, 2020 in European Patent Application No. 16841682.4 filed Aug. 25, 2016.
Mou, Tiantian, et al., "*Preparation and biodistribution of [18F]FP20P as myocardial perfusion imaging agent for positron emission tomography*",Bioorganic & Medicinal Chemistry, 2010, 18(3), pp. 1312-1320.
Djellal, Ahmed, et al., "*Synthesis of S-benzyl thioethers of propylboronic acids, Phosphorus, Sulfur and Silicon and the Related Elements*", 2004, 179(6), pp. 1123-1129.
Chu, Hsuan-Chih, et al., "*Novel Reversible Chemosensory Material Based on Conjugated Side-Chain Polymer Containing Fluorescent Pyridyl Receptor Pendants*", Journal of Physical Chemistry B, 2011, 115(28), pp. 8845-8852.
Dodd, Dharmpal S., et al., "*Synthesis of partially non-peptidic neurotensin mimetics*", Bioorganic & Medicinal Chemistry Letters, 1994, 4(10), pp. 1241-1246.
Kimani, Solomon M., et al., "*Multihydroxyl End Functional Polyethylenes: Synthesis, Bulk and Interfacial Properties of Polymer Surfactants*", Macromolecules, 2014, 47 (6), pp. 2062-2071.
Elias, Xavier, et al., "*Hybrid-Bridged Silsesquioxane as Recyclable Metathesis Catalyst Derived from a Bis-Silyated Hoveyda-Type Ligand*", Advanced Synthesis & Catalysis, 2006, 348(6), pp. 751-762.
Picaud, Sarah, et al., "*RVX-208, an inhibitor of BET transcriptional regulators with selectivity for the second bromodomain*", Proceedings of the National Academy of Sciences of the United States of America, 2013, 110(49), pp. 19754-19759.
Bourne, Gregory T., et al. "*A Backbone Linker for BOC-Based Peptide Synthesis and On-Resin Cyclization: Synthesis of Stylostatin I*", J. Org. Chem. 1999, 64(9) pp. 3095-3101.
International Search Report dated Nov. 15, 2016 in PCT/JP2016/074888, filed on Aug. 25, 2016.
Yasuyuki Yamada, et al., "Repetitive stepwise rotaxane formation toward programmable molecular arrays", Chemical Communications, 2013, vol. 94, pp. 11053-11055.
Office Action dated Sep. 1, 2020 in corresponding Chinese Patent Application No. 201680050461.7.

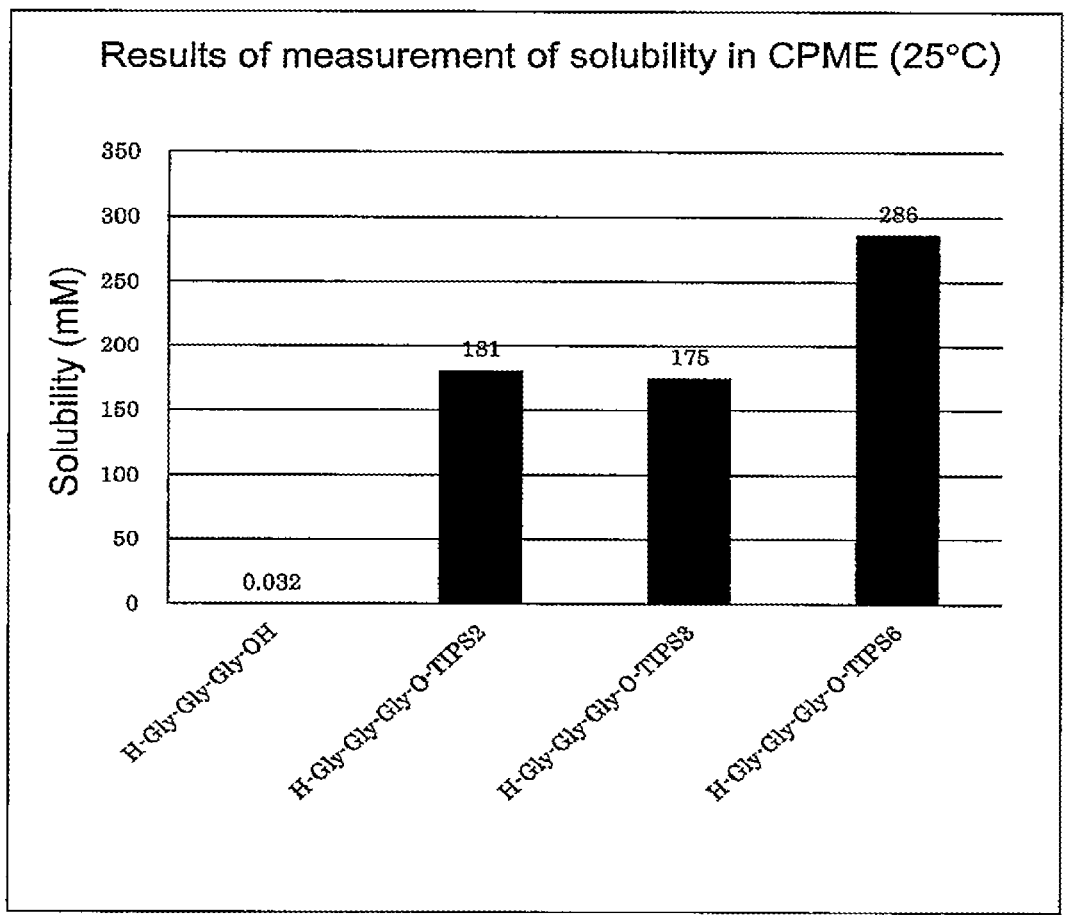

BENZYL COMPOUND

FIELD OF THE INVENTION

The present invention relates to a novel benzyl compound which is useful as a protecting agent for functional groups such as a carboxy group, a hydroxy group, a diol group, an amino group, and a mercapto group.

BACKGROUND OF THE INVENTION

In synthesis of peptides or a variety of compounds, the reaction is sometimes required to be performed by protecting the functional groups, such as a carboxy group and an amino group. Such a protecting group is desirably a group which can perform protection by a simple method and can be eliminated under mild conditions. For example, a tert-butoxycarbonyl group (Boc), a benzyloxycarbonyl group (Cbz), and a 9-fluorenylmethyloxycarbonyl group (Fmoc) are known as protecting groups for an amino group; and benzyl esters (Bn) and tert-butyl esters are known as protecting groups for a carboxy group. Recently, it has been reported that a benzyl alcohol compound is useful as a protecting group (Patent Document 1).

CITATION LIST

Patent Document

[Patent Document 1] WO 2012/029794

SUMMARY OF THE INVENTION

Problem to be Solved by the Invention

However, a compound having a functional group protected by a known protecting group has a disadvantage of being apt to precipitate. In particular, in peptide synthesis, since the compound is insoluble even in an organic solvent, it is often difficult to separate and purify the compound after the reaction. This difficulty in separation and purification is a serious problem in peptide synthesis serially performing condensation reactions.

An object of the present invention is therefore to provide a protecting group which enhances the solubility of a compound in which a functional group is protected by the protecting group in an organic solvent and thereby facilitates the separation and purification of the protecting group after a reaction with avoiding solidification or insolubilization.

Means for Solving the Problem

Accordingly, the present inventors investigated a variety of substituents of benzyl compounds represented by benzyl alcohol, and as a result, found that a compound in which a functional group is protected by a compound including a benzene ring having a trialkylsilyloxy group via an oxyalkylene group is hardly precipitated and is easily separated and purified by a liquid-liquid phase separation procedure and that the latter compound is useful as a protecting agent, and have accomplished the present invention.

That is, the present invention provides the following aspects [1] to [5]:

[1] A benzyl compound represented by Formula (1):

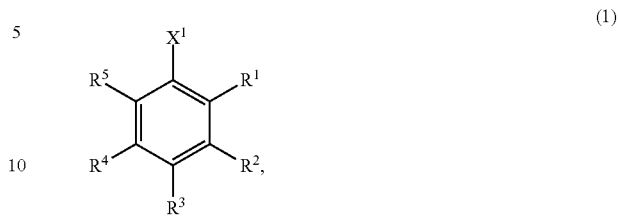

where $X^1$ represents —CH$_2$OR$^{14}$ (where $R^{14}$ represents a hydrogen atom, a halogenocarbonyl group, or an active ester-type protecting group), —CH$_2$NHR$^{15}$ (where $R^{15}$ represents a hydrogen atom, a linear or branched alkyl group having 1 to 6 carbon atoms, or an aralkyl group), a halogenomethyl group, a methyl azide group, a formyl group, or an oxime; and at least one of $R^1$, $R^2$, $R^3$, $R^4$, and $R^5$ is a group represented by Formula (2):

$$—O—R^6—X^2-A \quad (2), \text{ and}$$

the remainders each represent a hydrogen atom, a halogen atom, an alkyl group having 1 to 4 carbon atoms, or an alkoxy group having 1 to 4 carbon atoms, wherein $R^6$ represents a linear or branched alkylene group having 1 to 16 carbon atoms;

$X^2$ represents O or CONR$^{16}$ (where $R^{16}$ represents a hydrogen atom or an alkyl group having 1 to 4 carbon atoms); and A represents Formula (3), (4), (5), (6), (7), (8), (9), (10), (11), (12), or (13)

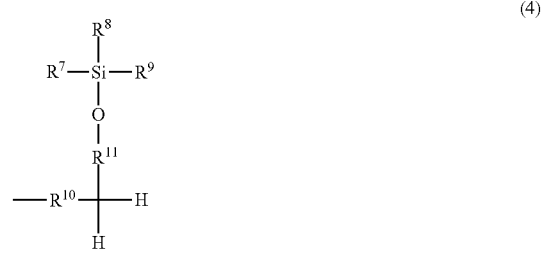

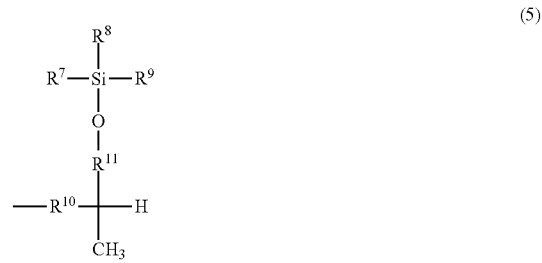

(6)
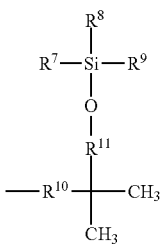

(7)
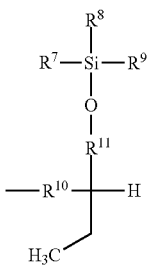

(8)
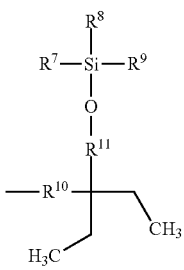

(9)
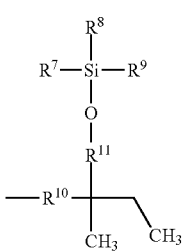

(10)
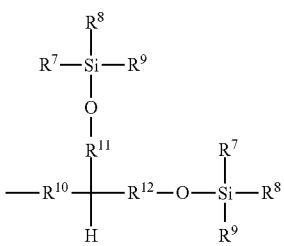

(11)
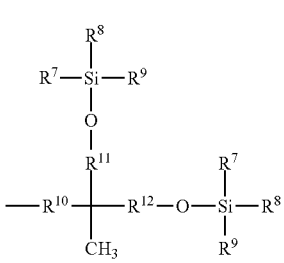

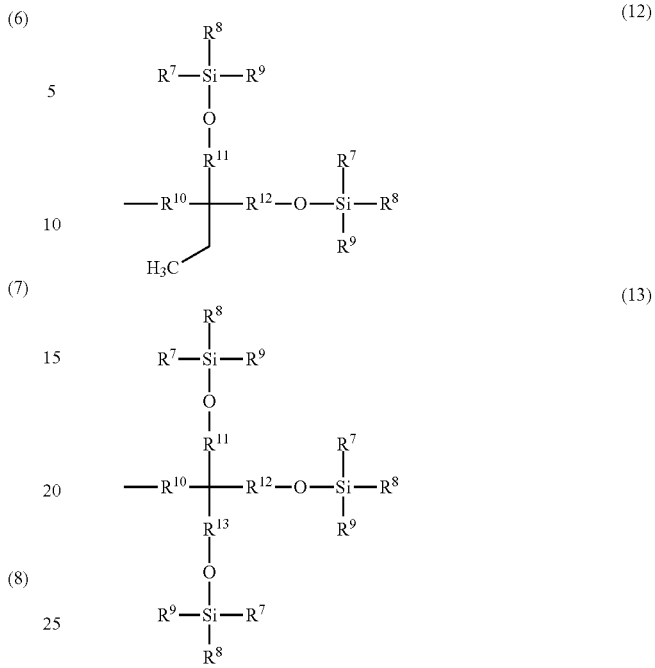

(where $R^7$, $R^8$, and $R^9$ are the same or different and each represent a linear or branched alkyl group having 1 to 6 carbon atoms or an optionally substituted aryl group; $R^{10}$ represents a single bond or a linear or branched alkylene group having 1 to 3 carbon atoms; and $R^{11}$, $R^{12}$, and $R^{13}$ each represent a linear or branched alkylene group having 1 to 3 carbon atoms);

[2] The benzyl compound according to aspect [1], wherein $X^1$ is —$CH_2OR^{14}$ (where $R^{14}$ represents a hydrogen atom, a halogenocarbonyl group, or an active ester-type protecting group), —$CH_2NHR^{15}$ (where $R^{15}$ represents a hydrogen atom, a linear or branched alkyl group having 1 to 6 carbon atoms, or an aralkyl group), or a halogenomethyl group;

[3] The benzyl compound according to aspect [1] or [2], wherein $R^6$ is a linear or branched alkylene group having 2 to 16 carbon atoms;

[4] The benzyl compound according to any one of aspects [1] to [3], wherein $R^6$ is a linear or branched alkylene group having 6 to 16 carbon atoms;

[5] The benzyl compound according to any one of aspects [1] to [4], wherein $R^{10}$ is a single bond or a methylene group; and $R^{11}$, $R^{12}$, and $R^{13}$ are methylene groups; and

[6] A protecting agent for a carboxy group, a hydroxy group, a diol group, an amino group, or a mercapto group, the protecting agent comprising the benzyl compound according to any one of aspects [1] to [5].

Effects of the Invention

A compound in which a functional group is protected by the benzyl compound (1) of the present invention tends to be in a liquid state and has enhanced solubility in a solvent, and is therefore readily separated and purified after the condensation reaction by a procedure such as liquid-liquid phase separation. In addition, the procedure of eliminating the protecting group is also easy.

If insolubilization or solidification of a raw material or an intermediate is an obstacle in the processes of producing various chemicals, such as medicines and agrochemicals, such a problem can be solved by combining the benzyl compound (1) of the present invention to the raw material or the intermediate to enhance the solubility thereof.

BRIEF DESCRIPTION OF THE DRAWINGS

FIG. 1 shows the results of measurement of solubility in cyclopentyl methyl ether (CPME).

DESCRIPTION OF THE EMBODIMENTS

The benzyl compound of the present invention represented by Formula (1) is characterized in that at least one of $R^1$ to $R^5$ has a structure represented by Formula (2). By having such a structure, the compound in which a functional group is protected by the benzyl compound (1) of the present invention tends to be in a liquid state, and the solubility thereof in a solvent is significantly enhanced.

In Formula (1), $X^1$ represents —$CH_2OR^{14}$ (where $R^{14}$ represents a hydrogen atom, a halogenocarbonyl group, or an active ester-type protecting group), —$CH_2NHR^{15}$ (where $R^{15}$ represents a hydrogen atom, a linear or branched alkyl group having 1 to 6 carbon atoms, or an aralkyl group), a halogenomethyl group, a methyl azide group, a formyl group, or an oxime.

Herein, examples of the halogen atom include a fluorine atom, a bromine atom, a chlorine atom, and an iodine atom.

Examples of the active ester-type protecting group include an active ester-type carbonyl group and an active ester-type sulfonyl group. Examples of the active ester-type carbonyl group include carbonyloxy succinimide, an alkoxycarbonyl group, an aryloxycarbonyl group, and an aralkyloxycarbonyl group, and more preferred examples include carbonyloxy succinimide.

Examples of the active ester-type sulfonyl group include an alkylsulfonyl group and an arylsulfonyl group, and more preferred examples include a $C_1$-$C_6$ alkylsulfonyl group and a p-toluenesulfonyl group.

Examples of the linear or branched alkyl group having 1 to 6 carbon atoms represented by $R^{15}$ include a methyl group, an ethyl group, and an n-propyl group. Examples of the aralkyl group include a phenyl $C_{1-4}$ alkyl group, such as a benzyl group.

$X^1$ is preferably —$CH_2OR^{14}$ (where $R^{14}$ is the same as the above) or —$CH_2NHR^{15}$ (where $R^{15}$ is the same as above) and is more preferably a hydroxymethyl group or an aminomethyl group.

In the benzyl compound of the present invention, at least one of $R^1$ to $R^5$ is a group represented by Formula (2). Preferably one to four, more preferably one to three of $R^1$ to $R^5$ is a group represented by Formula (2). The remainders are each a hydrogen atom, a halogen atom, an alkyl group having 1 to 4 carbon atoms, or an alkoxy group having 1 to 4 carbon atoms.

Herein, examples of the halogen atom as the remainder represented by $R^1$ to $R^5$ include a fluorine atom, a chlorine atom, and a bromine atom. Among these atoms, a fluorine atom and a chlorine atom are preferred. Examples of the alkoxy group having 1 to 4 carbon atoms as the remainder include a methoxy group, an ethoxy group, an n-propyloxy group, an isopropyloxy group, and an n-butyloxy group. Among these groups, a methoxy group is preferred. Examples of the alkyl group having 1 to 4 carbon atoms include a methyl group, an ethyl group, an n-propyl group, an isopropyl group, and an n-butyl group. Among these groups, a methyl group is preferred.

$R^6$ represents a linear or branched alkylene group having 1 to 16 carbon atoms. The number of carbon atoms of the alkylene group is preferably 2 or more, more preferably 6 or more, and most preferably 8 or more and preferably 16 or less, more preferably 14 or less, and most preferably 12 or less, from the viewpoint of improving the solubility of the compound combined to the benzyl compound (1) of the present invention in a solvent.

The alkylene group is preferably a linear or branched alkylene group having 2 to 16 carbon atoms, more preferably a linear or branched alkylene group having 6 to 16 carbon atoms, more preferably a linear or branched alkylene group having 8 to 14 carbon atoms, and most preferably a linear or branched alkylene group having 8 to 12 carbon atoms. Examples of the alkylene group include a methylene group, an ethylene group, a trimethylene group, a tetramethylene group, a pentamethylene group, a hexamethylene group, a heptamethylene group, an octamethylene group, a nanomethylene group, a decamethylene group, an undecamethylene group, a dodecamethylene group, and a tetradecamethylene group.

$X^2$ represents O or $CONR^{16}$. $R^{16}$ represents a hydrogen atom or an alkyl group having 1 to 4 carbon atoms and is preferably a hydrogen atom.

A is a group represented by Formula (3), (4), (5), (6), (7), (8), (9), (10), (11), (12), or (13), where $R^7$, $R^8$, and $R^9$ are the same or different and each represent a linear or branched alkyl group having 1 to 6 carbon atoms or an optionally substituted aryl group. Herein, examples of the linear or branched alkyl group having 1 to 6 carbon atoms include a methyl group, an ethyl group, an n-propyl group, an isopropyl group, an n-butyl group, an isobutyl group, a sec-butyl group, a tert-butyl group, an n-pentyl group, and an n-hexyl group. Among these groups, an alkyl group having 1 to 4 carbon atoms is more preferred, and a methyl group, a tert-butyl group, and an isopropyl group are further preferred.

Examples of the optionally substituted aryl group include an aryl group having 6 to 10 carbon atoms, specifically, a phenyl group or naphthyl group optionally substituted with an alkyl group having 1 to 3 carbon atoms. In particular, a phenyl group is preferred.

$R^{10}$ represents a single bond or a linear or branched alkylene group having 1 to 3 carbon atoms. Examples of the linear or branched alkylene group having 1 to 3 carbon atoms include a methylene group, an ethylene group, a trimethylene group, and a propylene group. Among these alkylene groups, a methylene group is particularly preferred.

$R^{11}$, $R^{12}$, and $R^{13}$ each represent a linear or branched alkylene group having 1 to 3 carbon atoms. Examples of the linear or branched alkylene group having 1 to 3 carbon atoms include a methylene group, an ethylene group, a trimethylene group, and a propylene group, and a methylene group is particularly preferred.

In a more preferred compound represented by Formula (1), $X^1$ is —$CH_2OR^{14}$ (where $R^{14}$ is the same as above), —$CH_2NHR^{15}$ (where $R^{15}$ is the same as above), or a halogenomethyl group; one to three of $R^1$, $R^2$, $R^3$, $R^4$, and $R^5$ are the group represented by Formula (2), and the remainders are each a hydrogen atom, an alkyl group having 1 to 4 carbon atoms, or an alkoxy group having 1 to 4 carbon atoms; $R^6$ is a linear or branched alkylene group having 2 to 16 carbon atoms (more preferably a linear or branched alkylene group having 6 to 16 carbon atoms, and most preferably a linear or branched alkylene group having 8 to 14 carbon atoms); $X^2$ is O or CONH; $R^{10}$ is a single bond or a methylene group; and $R^{11}$, $R^{12}$, and $R^{13}$ are methylene groups.

The structure represented by Formula (1) in which $X^1$ and $R^1$ to $R^5$ are substituted is preferably, for example, the following structure:

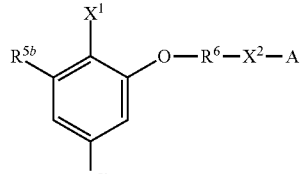
(1-1)

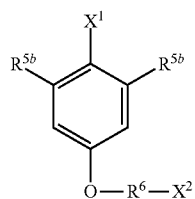
(1-2)

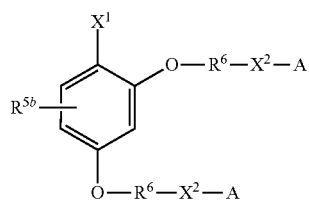
(1-3)

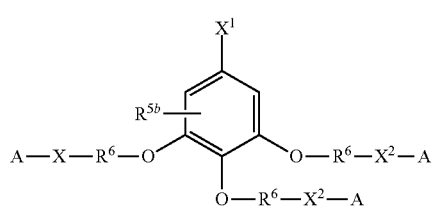
(1-4)

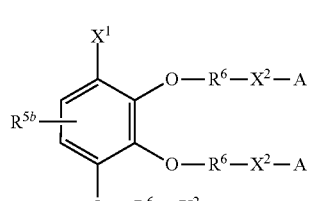
(1-5)

(where $R^{5b}$ represents a hydrogen atom, a halogen atom, an alkyl group having 1 to 4 carbon atoms, or an alkoxy group having 1 to 4 carbon atoms; and $X^1$, $X^2$, $R^6$, and A are the same as above).

Examples of the benzyl compound (1) of the present invention include the following (a) to (h).

(a) TIPS2-OP-Type Protecting Agent

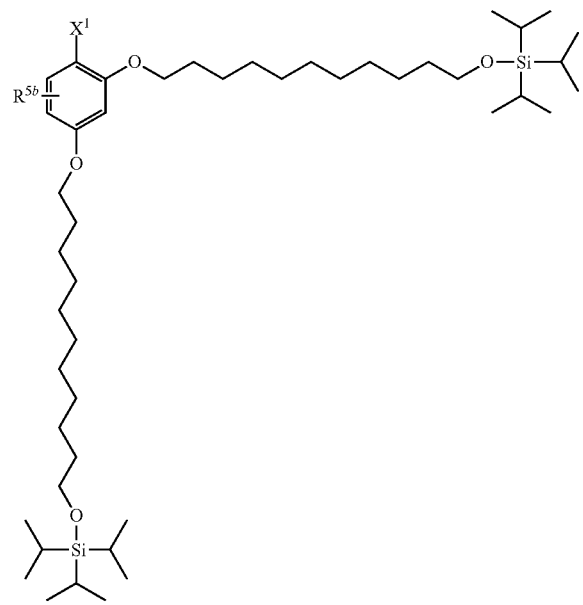

(where $X^1$ represents —$CH_2OR^{14}$ (where $R^{14}$ represents a hydrogen atom, a halogenocarbonyl group, or an active ester-type protecting group), —$CH_2NHR^{15}$ (where $R^{15}$ is the same as above), a halogenomethyl group, a methyl azide group, a formyl group, or an oxime; and $R^{5b}$ represents a hydrogen atom, a halogen atom, an alkyl group having 1 to 4 carbon atoms, or an alkoxy group having 1 to 4 carbon atoms).

(b) TIPS3-OMP-Type Protecting Agent

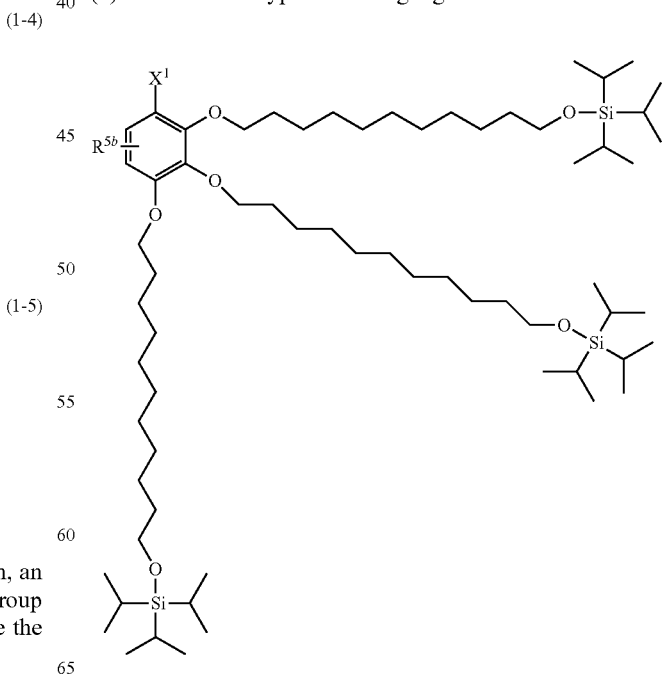

(where $X^1$ and $R^{5b}$ are the same as those in (a)).

(c) TIPS3-MMP-Type Protecting Agent
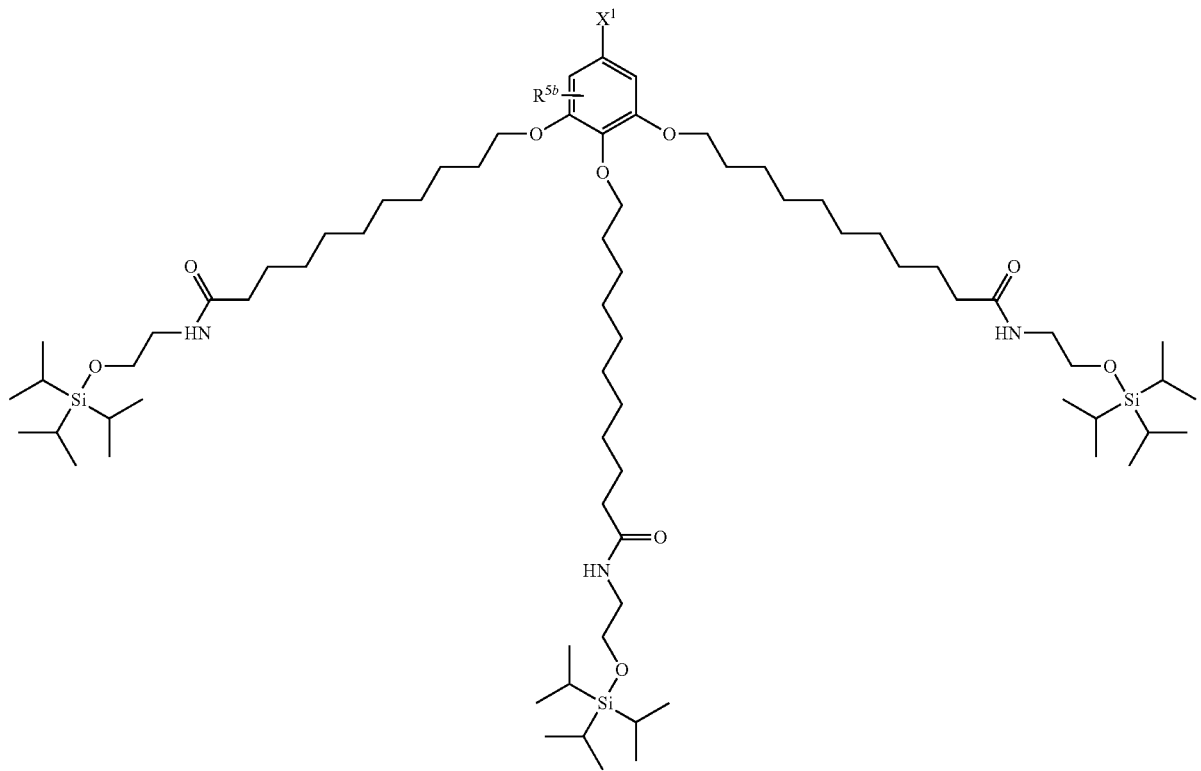
(where $X^1$ and $R^{5b}$ are the same as those in (a)).
(d) TIPS3-O-Type Protecting Agent
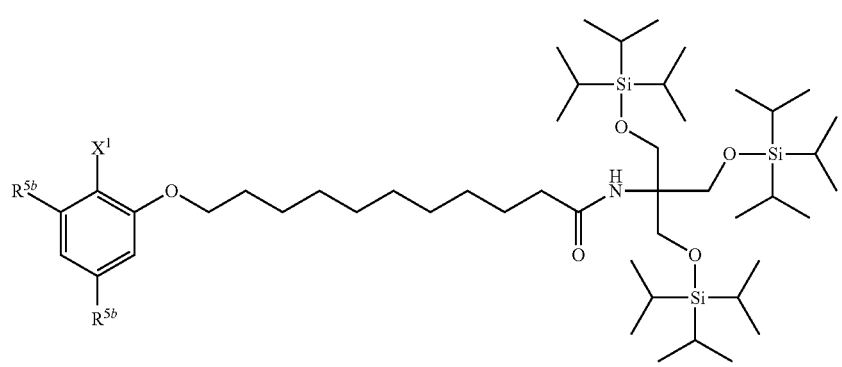
(where, $X^1$ and $R^{5b}$ are the same as those in (a)).

(e) TIPS6-OP-Type Protecting Agent
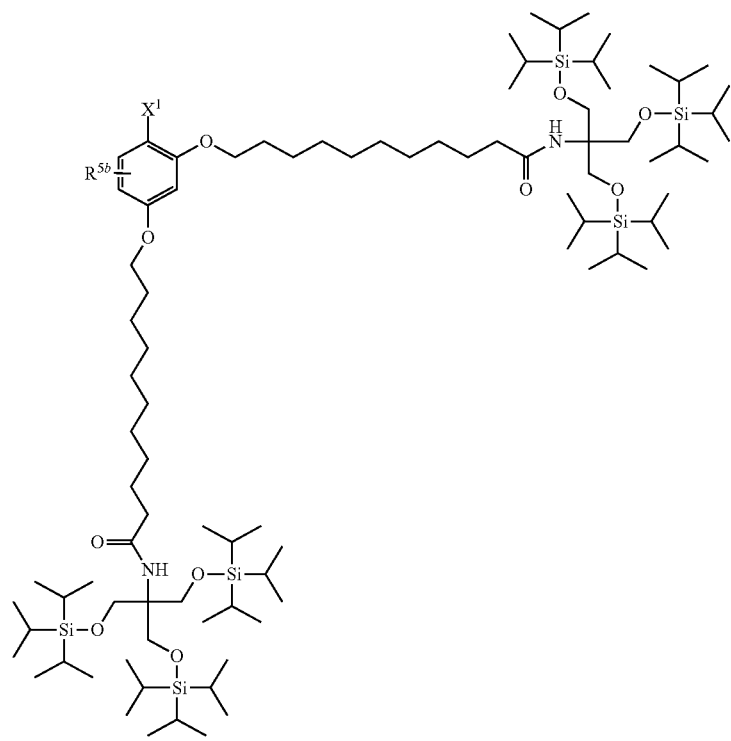
(where $X^1$ and $R^5$ are the same as those in (a)).
(f) TIPS6-MMP-Type Protecting Agent
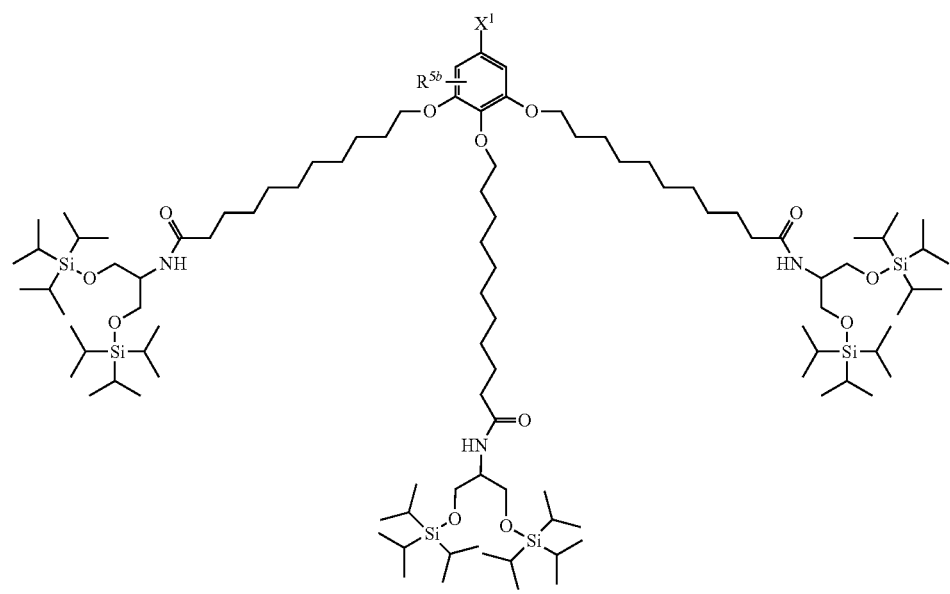
(where $X^1$ and $R^{5b}$ are the same as those in (a)).

(g) TIPS9-OMP-Type Protecting Agent

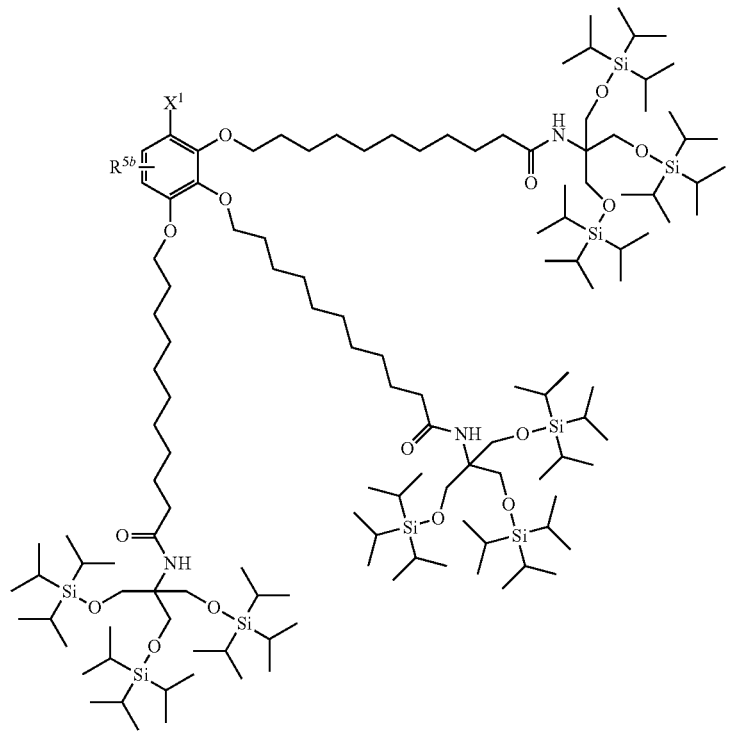

(where $X^1$ and $R^{5b}$ are the same as those in (a)).

(h) TBDPS2-OP-Type Protecting Agent

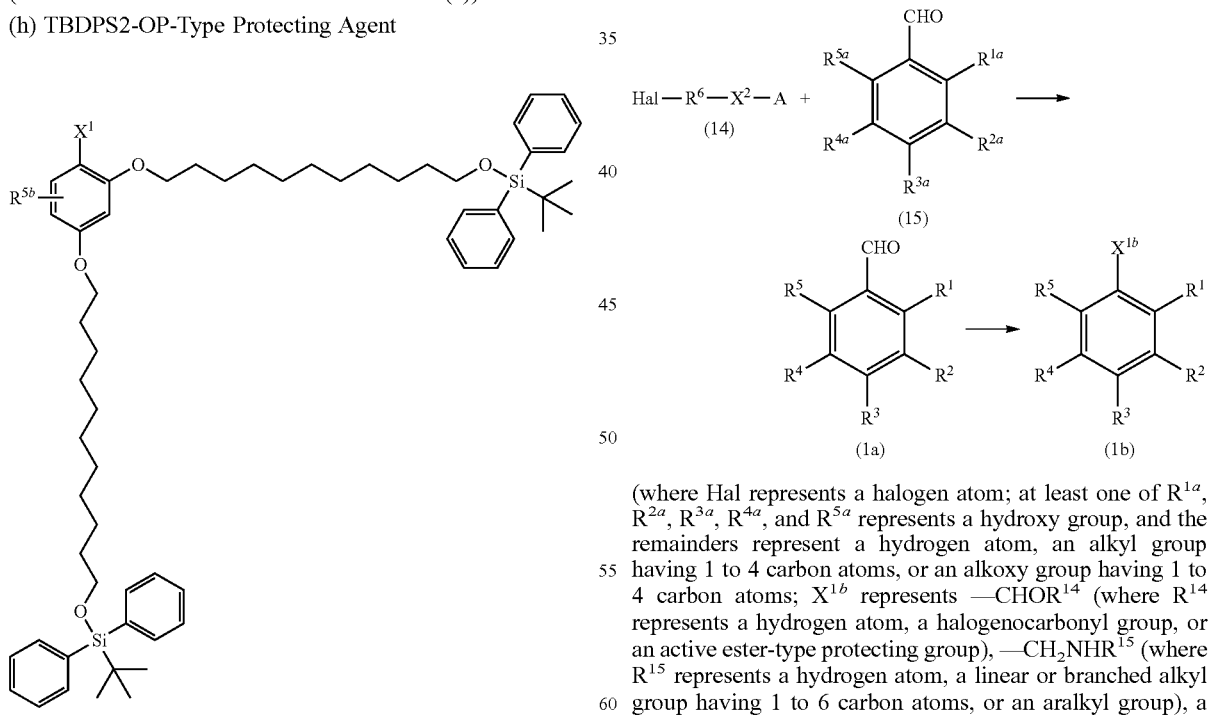

(where $X^1$ and $R^{5b}$ are the same as those in (a)).

The benzyl compound (1) of the present invention can be produced, for example, according to the following reaction scheme:

(where Hal represents a halogen atom; at least one of $R^{1a}$, $R^{2a}$, $R^{3a}$, $R^{4a}$, and $R^{5a}$ represents a hydroxy group, and the remainders represent a hydrogen atom, an alkyl group having 1 to 4 carbon atoms, or an alkoxy group having 1 to 4 carbon atoms; $X^{1b}$ represents —CHOR$^{14}$ (where R$^{14}$ represents a hydrogen atom, a halogenocarbonyl group, or an active ester-type protecting group), —CH$_2$NHR$^{15}$ (where R$^{15}$ represents a hydrogen atom, a linear or branched alkyl group having 1 to 6 carbon atoms, or an aralkyl group), a halogenomethyl group, a methyl azide group, or an oxime; and $R^1$ to $R^6$, $X^2$, and A are the same as above).

That is, silyloxylated alkyl halide (14) and a benzaldehyde (15) are reacted to obtain a silyloxylated benzaldehyde (1a). The formyl group is then converted into another substituent, such as a hydroxymethyl group, to obtain a benzyl compound (1b).

The silyloxylated alkyl halide (14) as a raw material can be produced by, for example, reacting a halogenated alcohol and a silylating agent in the presence of a base. Examples of the halogen atom in Formula (14) include a chlorine atom.

Examples of the silylating agent used in the above-mentioned reaction include triisopropylsilyl chloride (TIPSCl), triisopropylsilyl bromide, triisopropylsilyl iodide, methanesulfonyl triisopropylsilyl, trifluoromethanesulfonyl isopropylsilyl, p-toluenesulfonyl triisopropylsilyl, and tert-butyldiphenylchlorosilane (TBDPSCl).

Examples of the base include organic bases, such as TEA, DIPEA, DBU, diazabicyclononene (DEN), DABCO, imidazole, N-methylimidazole, N,N-dimethylaniline, pyridine, 2,6-lutidine, DMAP, LDA, NaOAc, MeONa, MeOK, lithium hexamethyldisilazide (LHMDS), and sodium bis(trimethylsilyl)amide (NaHMDS); and inorganic bases, such as $Na_2CO_3$, $NaHCO_3$, NaH, $NaNH_2$, $K_2CO_3$, $Cs_2CO_3$, $AgNO_3$, and $Pb(NO)_2$.

Examples of the solvent include hydrocarbons, such as hexane and heptane; ethers, such as diethyl ether, diisopropyl ether, cyclopentyl methyl ether (CPME), tetrahydrofuran, and dioxane; nitriles, such as acetonitrile; amides, such as dimethylformamide, dimethylacetamide, and hexamethylphosphoramide; sulfoxides, such as dimethyl sulfoxide; lactams, such as N-methylpyrrolidone; halogenated hydrogens, such as chloroform and dichloromethane (DCM); aromatic hydrocarbons, such as toluene and xylene; and solvent mixtures thereof.

The reaction may be performed, for example, at 0° C. to 100° C. for 1 to 24 hours.

The reaction of the silyloxylated alkyl halide (14) and the benzaldehyde (15) is preferably performed in the presence of a base.

Examples of the base used in the reaction include organic bases, such as TEA, DIPEA, DBU, DBN, DABCO, imidazole, N-methylimidazole, N,N-dimethylaniline, pyridine, 2,6-lutidine, DMAP, LDA, NaOAc, MeONa, MeOK, lithium hexamethyldisilazide (LHMDS), and sodium bis(trimethylsilyl)amide (NaHMDS); and inorganic bases, such as $Na_2CO_3$, $NaHCO_3$, NaH, $K_2CO_3$, $Cs_2CO3$, $AgNO3$, and $Pb(NO_3)_2$.

Examples of the solvent include hydrocarbons, such as hexane and heptane; ethers, such as diethyl ether, diisopropyl ether, CPME, tetrahydrofuran, and dioxane; nitriles, such as acetonitrile; amides, such as dimethylformamide, dimethylacetamide, and hexamethylphosphoramide; sulfoxides, such as dimethyl sulfoxide; lactams, such as N-methylpyrrolidone; halogenated hydrogens, such as chloroform and dichloromethane (DCM); aromatic hydrocarbons, such as toluene and xylene; and solvent mixtures thereof.

The reaction may be performed, for example, at 40° C. to 150° C. for 1 to 24 hours.

The method for converting the formyl group of the compound represented by Formula (1a) into a compound represented by Formula (1b) where $X^{1b}$ is hydroxymethyl is, for example, a reducing process. The reducing process preferably uses a reducing agent.

Examples of the reducing agent include lithium borohydride, sodium borohydride, lithium aluminum hydride, and aluminum hydride. Examples of the solvent include hydrocarbons, such as hexane and heptane; alcohols, such as methanol and ethanol; ethers, such as diethyl ether, diisopropyl ether, CPME, tetrahydrofuran, and dioxane; aromatic hydrocarbons, such as toluene and xylene; and solvent mixtures thereof. The reaction may be performed, for example, at 0° C. to 90° C. for 1 to 24 hours.

The compound represented by Formula (1b) where $X^{1b}$ is an aminomethyl group can be obtained by converting the hydroxymethyl group into an azidomethyl group and reducing the azidomethyl group. The method for azidation preferably uses diphenylphosphoryl azide.

Examples of the base include organic bases, such as DBU, DBN, TEA, DIPEA, and DABCO. Examples of the solvent include hydrocarbons, such as hexane and heptane; ethers, such as diethyl ether, diisopropyl ether, CPME, tetrahydrofuran, and dioxane; aromatic hydrocarbons, such as toluene and xylene; and solvent mixtures thereof. The reaction may be performed, for example, at 0° C. to 100° C. for 1 to 24 hours.

Examples of the reducing process include a Staudinger reaction of reacting triphenylphosphine in the presence of water and catalytic hydrogenation. Preferred is the Staudinger reaction.

Examples of the solvent for the Staudinger reaction include hydrocarbons, such as hexane and heptane; ethers, such as diethyl ether, diisopropyl ether, CPME, tetrahydrofuran, and dioxane; aromatic hydrocarbons, such as toluene and xylene; and solvent mixtures thereof. The reaction may be performed, for example, at 20° C. to 100° C. for 1 to 24 hours.

The compound represented by Formula (1b) where $X^{1b}$ is a halogenated methyl group can be produced by, for example, reacting a halogenating reagent to a hydroxymethyl group in the presence of a base. Examples of the halogen atom of $X^{1b}$ include a chlorine atom.

Examples of the halogenating reagent include thionyl chloride, acetyl chloride, acetyl bromide, triphenylphosphine/carbon tetrachloride, and triphenylphosphine/carbon tetrabromide.

Examples of the base include organic bases, such as pyridine, TEA, DIPEA, DBU, DBN, and DABCO.

Examples of the solvent include hydrocarbons, such as hexane and heptane; ethers, such as diethyl ether, diisopropyl ether, CPME, tetrahydrofuran, and dioxane; aromatic hydrocarbons, such as toluene and xylene; and solvent mixtures thereof. The reaction may be performed, for example, at 0° C. to 100° C. for 0.5 to 24 hours.

The compound represented by Formula (1b) where $X^{1b}$ is a halogenocarbonyl oxymethyl group can be obtained by chloroformylating a hydroxymethyl group with phosgene or triphosgene in the presence of a base. Preferred is a method of using triphosgene.

Examples of the base include organic bases, such as pyridine, TEA, DIPEA, 2,6-lutidine, N,N-dimethylaniline, DBU, DBN, and DABCO.

Examples of the solvent include hydrocarbons, such as hexane and heptane; ethers, such as diethyl ether, diisopropyl ether, CPME, tetrahydrofuran, and dioxane; aromatic hydrocarbons, such as toluene and xylene; halogenated hydrogens, such as chloroform and dichloromethane (DCM), and solvent mixtures thereof. The reaction may be performed, for example, at −10° C. to 50° C. for 1 to 48 hours.

The compound represented by Formula (1b) where $X^{1b}$ is an N-succinimidyl carboxy-substituted oxymethyl group can be obtained by carbonate esterification a hydroxymethyl group with N,N'-disuccinimidyl carbonate or N,N'-disuccinimidyl oxalate in the presence of a base. The method preferably uses N,N'-disuccinimidyl carbonate.

Examples of the base include organic bases, such as TEA, DMAP, pyridine, DIPEA, 2,6-lutidine, N,N-dimethylaniline, DBU, DBN, and DABCO.

Examples of the solvent include hydrocarbons, such as hexane and heptane; ethers, such as diethyl ether, diisopropyl ether, cyclopentyl methyl ether (CPME), tetrahydrofuran, and dioxane; nitriles, such as acetonitrile; amides, such as dimethylformamide, dimethylacetamide, and hexamethylphosphoramide; sulfoxides, such as dimethyl sulfoxide; lactams, such as N-methylpyrrolidone; halogenated hydrogens, such as chloroform and dichloromethane (DCM); aromatic hydrocarbons, such as toluene and xylene; and solvent mixtures thereof. The reaction may be performed, for example, at 0° C. to 60° C. for 1 to 48 hours.

The compound represented by Formula (1b) where $X^{1b}$ is —$CH_2NHR^{15}$ (where $R^{15}$ is the same as above) can be obtained by, for example, reacting the formyl group in Formula (1a) and amine represented by $H_2N$—$R^{15}$ or its acid adduct salt under acid catalyst conditions and reducing with a reducing agent.

Examples of the acid adduct salt of the amine represented by $H_2N$—$R^{15}$ include a hydrochloride, a sulfate, an acetate, a trifluoroacetate, a methanesulfonate, a trifluoromethanesulfonate, and a p-toluenesulfonate.

Examples of the acid catalyst include acetic acid, formic acid, hydrochloric acid, sulfuric acid, trifluoroacetic acid, methanesulfonic acid, trifluoromethanesulfonic acid, and p-toluenesulfonic acid.

Examples of the reducing agent include 2-picoline borane, 5-ethyl-2-methylpyridine borane (PEMB), hydrogenated cyanoborohydride, and hydrogenated triacetoxyborohydride.

Examples of the solvent include hydrocarbons, such as hexane and heptane; ethers, such as diethyl ether, diisopropyl ether, cyclopentyl methyl ether (CPME), tetrahydrofuran, and dioxane; nitriles, such as acetonitrile; alcohols, such as methanol, ethanol, and propanol; aromatic hydrocarbons, such as toluene and xylene; and solvent mixtures thereof. The reaction may be performed, for example, at 0° C. to 50° C. for 0.5 to 24 hours.

The compound represented by Formula (1b) where $X^{1b}$ is an oxime can be obtained by reacting the formyl group in Formula (1a) and an acid adduct salt of hydroxylamine in the presence of a base.

Examples of the acid adduct salt of hydroxylamine include a hydrochloride, a sulfate, an acetate, a trifluoroacetate, a methanesulfonate, a trifluoromethanesulfonate, and a p-toluenesulfonate.

Examples of the base include organic bases, such as TEA, pyridine, DIPEA, N,N-dimethylaniline, DBU, DBN, and DABCO; and inorganic bases, such as sodium hydroxide, sodium bicarbonate, potassium hydroxide, and potassium carbonate.

Examples of the solvent include hydrocarbons, such as hexane and heptane; ethers, such as diethyl ether, diisopropyl ether, cyclopentyl methyl ether (CPME), tetrahydrofuran, and dioxane; halogenated hydrogens, such as chloroform and dichloromethane; aromatic hydrocarbons, such as toluene and xylene; and solvent mixtures thereof. The reaction may be performed, for example, at 0° C. to 50° C. for 1 to 48 hours.

The benzyl compound (1) of the present invention can be used as a protecting agent for a functional group, such as a carboxy group, a hydroxy group, an amino group, and a mercapto group. The compound in which the carbonyl group is protected by the benzyl compound (1) of the present invention is characterized by tending to be in a liquid state and its high solubility in a solvent. Accordingly, a compound in which a functional group is protected by the benzyl compound (1) of the present invention used as a protecting agent can be readily dissolved in an organic solvent and can be easily separated and purified by a procedure such as liquid-liquid phase separation. The protecting group used in the inventive compound can be readily eliminated by, for example, an acid or catalytic hydrogenation.

The compound which can be protected by the benzyl compound (1) of the present invention may be any compound having a functional group such as a carboxy group, a hydroxy group, a diol group, and an amino group, and examples thereof include amino acids, peptides, saccharides, proteins, nucleotides, various medicinal compounds and agrochemical compounds, and various polymers and dendrimers.

The method of synthesizing a peptide using the benzyl compound (1) of the present invention as a protecting agent includes, for example, the following steps (1) to (4). In this peptide synthesizing method, the protected peptide obtained in each step and the target peptide can be separated by liquid-liquid separation. Accordingly, the method is particularly industrially advantageous.

(1) The benzyl compound (1) of the present invention is condensed with the C-terminal carboxy group of an N-protected amino acid or N-protected peptide in a soluble solvent to obtain an N-protected C-protected amino acid or N-protected C-protected peptide in which the C-terminal is protected by the benzyl compound (1) of the present invention.

(2) The protecting group on the N-terminal of the resulting N-protected C-protected amino acid or N-protected C-protected peptide is removed to obtain a C-protected amino acid or C-protected peptide.

(3) An N-protected amino acid or N-protected peptide is condensed with the N-terminal of the resulting C-protected amino acid or C-protected peptide to obtain an N-protected C-protected peptide.

(4) The protecting groups on the N-terminal and the protecting group on the C-terminal of the resulting N-protected C-protected peptide are removed to obtain the target peptide.

EXAMPLES

The present invention will now be described in detail by Examples, but the present invention is not limited thereto.

Example 1

Synthesis of TIPS2-OP-Type Protecting Agent

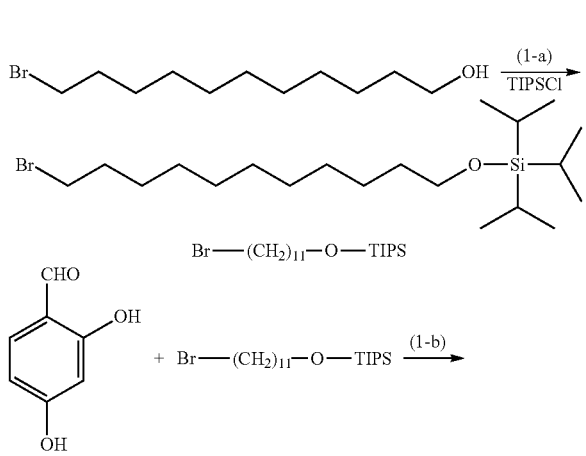

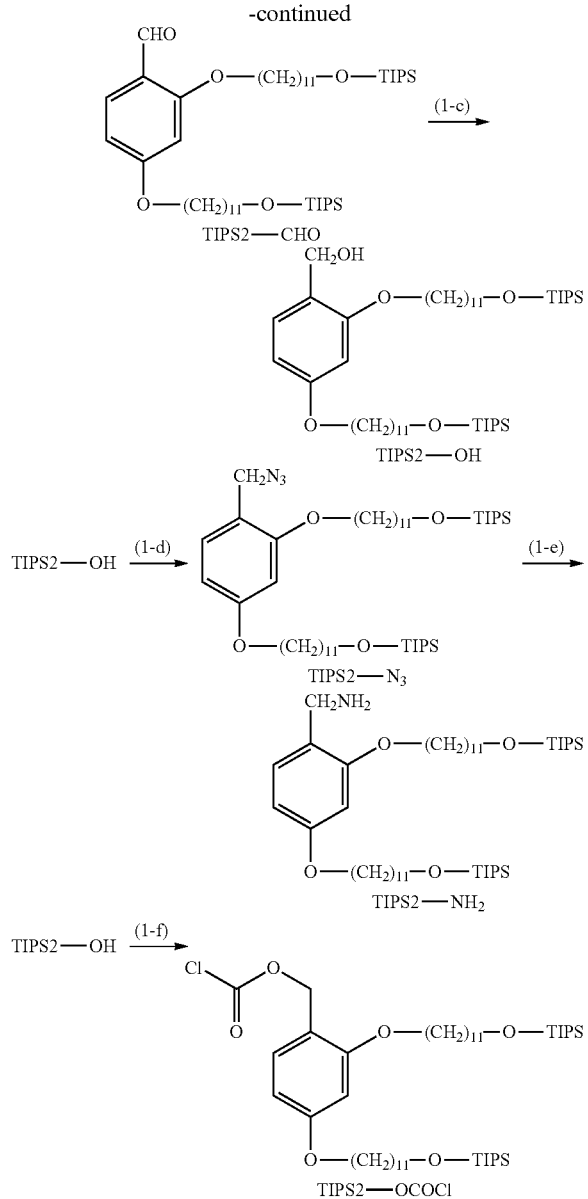

(Hereinafter, Br—(CH$_2$)$_{11}$—O-TIPS, TIPS2-CHO, TIPS2-OH, TIPS2-N$_3$, TIPS2-NH$_2$, and TIPS2-OCOCl indicate the respective structures in the drawing.)

Example (1-a)

1-Bromoundecanol (0.90 g, 3.58 mmol) was dissolved in dichloromethane (12.8 mL), and imidazole (0.61 g, 8.96 mmol) was added thereto. The mixture was cooled to 5° C., and TIPSCl (0.91 mL, 4.30 mmol) was dropwise added thereto. After 5 minutes, the mixture was warmed to room temperature and was stirred for 2 hours. CPME (51.2 mL) was added to the reaction solution, followed by washing with water (12.8 mL) once, 1 N hydrochloric acid (12.8 mL) once, and water (12.8 mL) three times. The solvent was distilled. The residue was dissolved in heptane (51.2 mL), followed by liquid-liquid extraction with acetonitrile (25.6 mL). Heptane (12.8 mL) was added to the resulting heptane layer, followed by liquid-liquid extraction with acetonitrile (25.6 mL). The liquid-liquid extraction with heptane and acetonitrile was further repeated once, and the solvent was then distilled to obtain Br—(CH$_2$)$_{11}$—O-TIPS (1.45 g, yield: 99.3%).

$^1$H-NMR (400 MHz, CDCl$_3$) δ 1.03-1.20 (m, 21H), 1.24-1.49 (m, 14H), 1.54 (quin., 2H), 1.85 (quin., 2H), 3.41 (t, 2H), 3.66 (t, 2H)

ESIMS MH+ 407.1

Example (1-b): TIPS2-CHO

Br—(CH$_2$)$_{11}$—O-TIPS (1.20 g, 2.95 mmol), 2,4-dihydroxybenzaldehyde (0.17 g, 1.23 mmol), and potassium carbonate (0.612 g, 4.43 mmol) were suspended in DMF (8.2 mL), and the suspension was heated to 85° C. and was stirred for 2 hours. The reaction solution was filtered, and the residue was washed with heptane (17.2 mL). The heptane layer was separated from the filtrate, and heptane (8.2 mL) was added to the layer, followed by liquid-liquid extraction with DMF (8.2 mL). The liquid-liquid extraction with heptane and DMF was further repeated once. Heptane (8.2 mL) was added to the resulting heptane layer, followed by washing with 1 N hydrochloric acid (8.2 mL) once, a 5% sodium bicarbonate aqueous solution (8.2 mL) once, and water (8.2 mL) once. Heptane (8.2 mL) was added to the resulting heptane layer, followed by liquid-liquid extraction with DMF (8.2 mL). Heptane (8.2 mL) was added to the resulting heptane layer, followed by liquid-liquid extraction with acetonitrile (8.2 mL). The solvent was distilled, and the resulting residue was purified by silica gel column chromatography (hexane:ethyl acetate=100:1) to obtain TIPS2-CHO (0.82 g, 84.2%).

$^1$H-NMR (400 MHz, CDCl$_3$) δ 1.03-1.06 (m, 42H), 1.20-1.39 (m, 28H), 1.40-1.56 (m, 4H), 1.73-1.86 (m, 4H), 3.64-3.68 (m, 4H), 3.96-4.04 (m, 4H), 6.41 (d, 1H), 6.48-6.52 (m, 1H), 7.79 (d, 1H), 10.33 (s, 1H)

$^{13}$C-NMR (100 MHz, CDCl$_3$) δ 12.2 (6C), 18.2 (12C), 26.0 (2C), 26.1, 26.2, 29.2-29.8 (12C), 33.2 (2C) 63.7 (2C), 68.6, 68.7, 99.1, 106.3, 119.1, 130.4, 163.5, 165.9, 188.6

ESIMS MH+ 791.6

Example (1-c): TIPS2-OH

TIPS2-CHO (0.49 g, 0.62 mmol) was dissolved in a mixed solution of THF (anhydrous, 4.7 mL) and methanol (0.24 mL). The solution was cooled to 5° C., and sodium borohydride (28 mg, 0.75 mmol) was added thereto, followed by stirring for 1 hour. The reaction was quenched with 1 N hydrochloric acid (0.59 mL), and CPME (12.3 mL) was added thereto, followed by liquid-liquid extraction with 1 N hydrochloric acid (3.7 mL) three times, a 5% sodium bicarbonate aqueous solution (3.7 mL) once, and water (3.7 mL) once. The solvent was distilled. The resulting residue was dissolved in heptane (12.3 mL), followed by liquid-liquid extraction with DMF (6.2 mL). Heptane (6.2 mL) was added to the resulting heptane layer, followed by liquid-liquid extraction with acetonitrile (6.2 mL). The liquid-liquid extraction with heptane and acetonitrile was further repeated once, and the solvent was then distilled to obtain TIPS2-OH (0.44 g, yield: 89.6%).

$^1$H-NMR (400 MHz, CDCl$_3$) δ 1.04-1.07 (m, 42H), 1.20-1.39 (m, 28H), 1.40-1.57 (m, 4H), 1.71-1.85 (m, 4H), 2.24 (t, 1H), 3.64-3.69 (m, 4H), 3.89-4.00 (m, 4H), 4.61 (d, 2H), 6.39-6.44 (m, 1H), 6.45 (d, 1H), 7.13 (d, 1H)

$^{13}$C-NMR (100 MHz, CDCl$_3$) δ 12.2 (6C), 18.2 (12C), 26.0 (2C), 26.2, 26.3, 29.4-29.8 (12C), 33.2 (2C), 62.2, 63.7 (2C), 68.2, 68.3, 100.0, 104.6, 121.9, 129.7, 158.3, 160.3

ESIMS MNa+ 815.6

Example (1-d): TIPS2-N$_3$

TIPS2-OH (0.85 g, 1.07 mmol) was dissolved in CPME (21.4 mL), and diphenylphosphoryl azide (0.69 mL, 3.21 mmol) and DBU (0.48 mL, 3.21 mmol) were added to the solution, followed by stirring at room temperature for 20 hours. The reaction solution was diluted with CPME (10.7 mL), followed by liquid-liquid extraction with a 5% sodium bicarbonate aqueous solution (21.4 mL) twice and water (21.4 mL) four times. The solvent was distilled, and the residue was dissolved in heptane (21.4 mL), followed by liquid-liquid extraction with DMF (10.7 mL). The liquid-liquid extraction with heptane and DMF was further repeated three times, and heptane (10.7 mL) was added to the heptane layer, followed by liquid-liquid extraction with acetonitrile (10.7 mL). The liquid-liquid extraction with heptane and acetonitrile was further repeated twice, and the solvent was then distilled to obtain TIPS2-N$_3$ (0.61 g, yield: 70.0%).

$^1$H-NMR (400 MHz, CDCl$_3$) δ 1.04-1.07 (m, 42H), 1.19-1.39 (m, 28H), 1.40-1.57 (m, 4H), 1.73-1.86 (m, 4H), 3.64-3.69 (m, 4H), 3.90-3.99 (m, 4H), 4.28 (s, 2H), 6.40-6.45 (m, 1H), 6.46 (d, 1H), 7.12 (d, 1H)

$^{13}$C-NMR (100 MHz, CDCl$_3$) δ 12.2 (6C), 18.2 (12C), 26.0 (2C), 26.2 (2C), 29.3-29.8 (12C), 33.2 (2C), 50.1, 63.7 (2C), 68.3 (2C), 99.9, 104.7, 116.4, 131.1, 158.4, 160.9

ESIMS MNa+ 840.8

Example (1-e): TIPS2-NH$_2$

TIPS2-N$_3$ (0.45 g, 0.55 mmol) was dissolved in toluene (11 mL), and triphenylphosphine (0.43 g, 1.66 mmol) and water (0.20 mL, 11.0 mmol) were added to the solution, followed by stirring at 60° C. for 3 hours. The solvent was distilled, and the residue was dissolved in heptane (11 mL), followed by liquid-liquid extraction with DMF (6 mL). The liquid-liquid extraction with heptane and DMF was further repeated twice, and heptane (11 mL) was then added to the heptane layer, followed by liquid-liquid extraction with acetonitrile (6 mL). The liquid-liquid extraction with heptane and acetonitrile was further repeated twice, and the solvent was then distilled to obtain TIPS2-NH$_2$ (0.39 g, yield: 89.5%).

$^1$H-NMR (400 MHz, CDCl$_3$) δ 1.04-1.07 (m, 42H), 1.20-1.39 (m, 28H), 1.40-1.58 (m, 4H), 1.72-1.84 (m, 4H), 2.14 (s, 2H), 3.64-3.69 (m, 4H), 3.77 (s, 2H), 3.90-3.98 (m, 4H), 6.38-6.41 (m, 1H), 6.44 (d, 1H), 7.08 (d, 1H)

$^{13}$C-NMR (100 MHz, CDCl$_3$) δ 12.2 (6C), 18.2 (12C), 26.0 (2C), 26.2, 26.4, 29.4-29.8 (12C), 33.2 (2C), 42.4, 63.7 (2C), 68.0, 68.3, 100.0, 104.5, 123.6, 129.3, 158.1, 159.8

ESIMS MNa+ 814.6

Example (1-f): TIPS2-OCOCl

Triphosgene (0.187 g, 0.63 mmol) was dissolved in dichloromethane (0.38 mL). The solution was cooled to −5° C., and a solution prepared by dissolving pyridine (0.15 mL, 1.89 mmol) and TIPS2-OH (1.00 g, 1.26 mmol) in dichloromethane (0.25 mL) was dropwise added to the solution. The mixture was stirred at −5° C. for 2 hours and then at room temperature for 17 hours. The solvent was distilled, and the residue was dissolved in hexane (5 mL), followed by filtration. The solvent of the filtrate was distilled to obtain TIPS2-OCOCl (0.95 g, yield: 88.0%).

ESIMS MH+ 855.8

Example (1-g): TIPS2-OSu

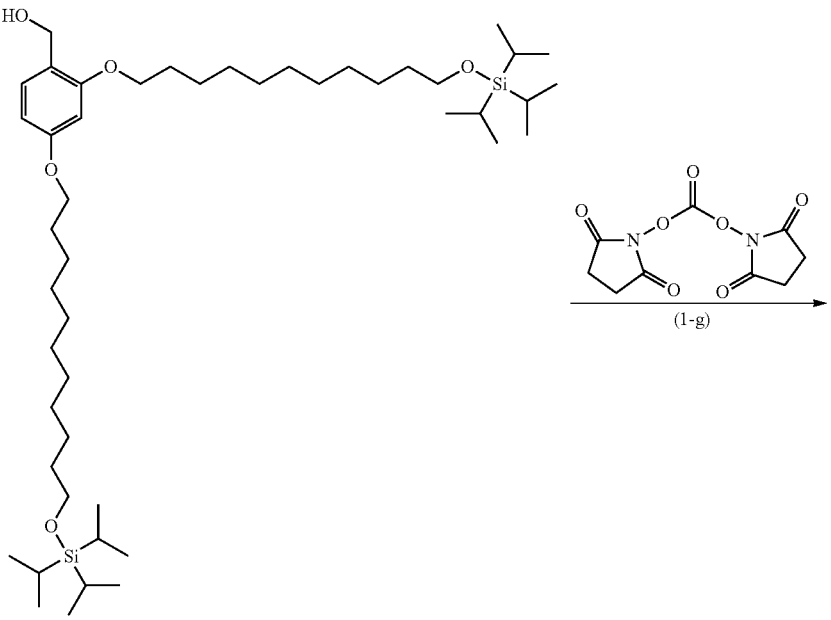

TIPS2—OH

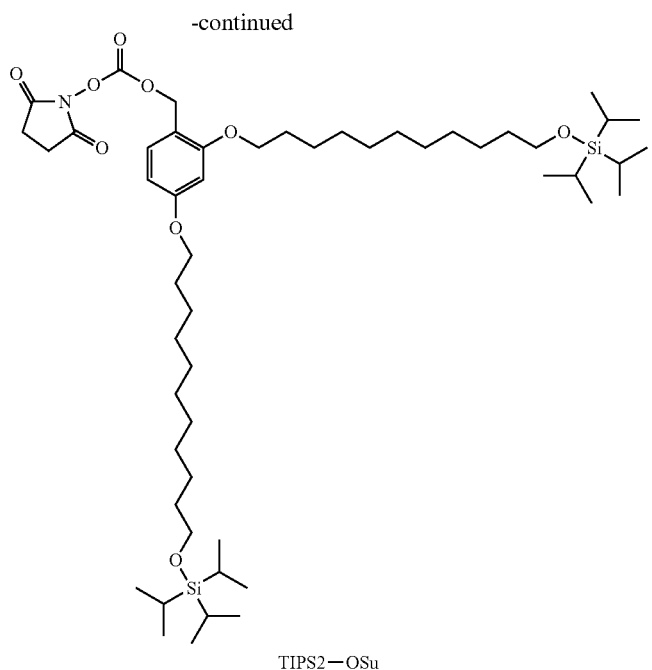

TIPS2—OSu (Hereinafter, TIPS2-OSu indicates the structure in the formula.)

N,N'-Disuccinimidyl carbonate (1.58 g, 6.15 mmol) was dissolved in acetonitrile (1.0 mL). The solution was cooled to 5° C., and a solution prepared by dissolving TIPS2-OH (0.24 g, 0.31 mmol) and TEA (1.1 mL, 7.63 mmol) in dichloromethane (1.0 mL) was dropwise added to the solution. The mixture was stirred at 5° C. for 5 minutes and then at room temperature for 4 hours. Dichloromethane (3.0 mL) was added to the reaction solution, followed by filtration. The solvent of the filtrate was distilled. THF (4.0 mL) was added to the resulting residue, and the solvent was distilled. The resulting residue was dissolved in heptane (8.0 mL), followed by liquid-liquid extraction with acetonitrile (8.0 mL). Heptane (4.0 mL) was added to the heptane layer, followed by liquid-liquid extraction with acetonitrile (8 mL) four times. Heptane (1.0 mL) was added to the resulting heptane layer, followed by liquid-liquid extraction with acetonitrile (8 mL). The solvent was then distilled to obtain TIPS2-OSu (34 mg, yield: 11.9%).

$^1$H-NMR (400 MHz, CDCl$_3$) δ 1.04-1.07 (m, 42H), 1.20-1.39 (m, 28H), 1.40-1.57 (m, 4H), 1.72-1.84 (m, 4H), 2.60 (s, 4H), 3.64-3.69 (m, 4H), 3.91-3.98 (m, 4H), 5.11 (s, 2H), 6.40-6.46 (m, 2H), 7.28 (d, 1H)

$^{13}$C-NMR (100 MHz, CDCl$_3$) δ 12.2 (6C), 18.2 (12C), 25.6 (2C), 26.0 (2C), 26.1, 26.2, 29.3-29.8 (12C), 33.2 (2C), 63.7 (2C), 68.2, 68.8, 73.3, 100.0, 105.1, 114.8, 133.3, 152.6, 159.5, 161.8, 171.3

Example (1-h): TIPS2-Cl

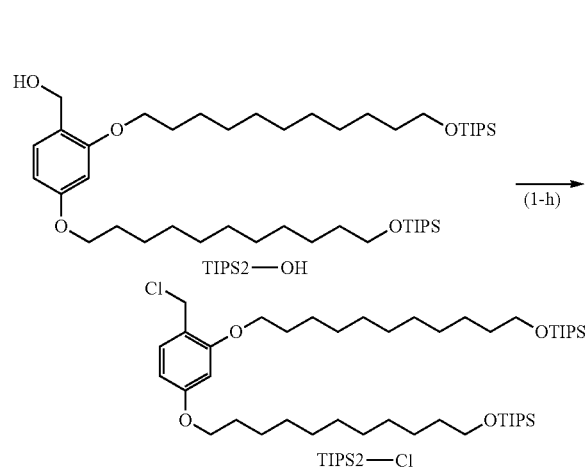

(Hereinafter, TIPS2-Cl indicates the structure in the formula.)

TIPS2-OH (0.42 g, 0.53 mmol) was dissolved in chloroform (8.5 mL), and DMF (8 μL, 0.11 mmol) and pyridine (95 μL, 1.18 mmol) were added to the solution. The mixture was cooled to 5° C., and thionyl chloride (78 μL, 1.07 mmol) was added thereto. The mixture was warmed to room temperature and was stirred for 1 hour. Heptane (25.2 mL) was added to the reaction solution, followed by liquid-liquid extraction with acetonitrile (25.2 mL). Heptane (4.2 mL) and CPME (1.3 mL) were added to the resulting heptane layer, followed by liquid-liquid extraction with acetonitrile (25.2 mL). Heptane (4.2 mL) was added to the resulting heptane layer, followed by liquid-liquid extraction with acetonitrile (25.2 mL). The liquid-liquid extraction with heptane and acetonitrile was further repeated once, and the heptane layer was concentrated under reduced pressure to obtain TIPS2-Cl (0.15 g).

$^1$H-NMR (400 MHz, Benzene-d$_6$) δ 1.12-1.16 (m, 42H), 1.23-1.49 (m, 28H), 1.56-1.73 (m, 8H), 3.61-3.73 (m, 8H), 4.61 (s, 2H), 6.35 (dd, 1H), 6.49 (d, 1H), 7.09 (d, 1H)

$^{13}$C-NMR (100 MHz, Benzene-d$_6$) δ 12.8 (6C), 18.7 (12C), 26.7 (3C), 26.9, 29.8-30.5 (12C), 33.9 (2C), 42.5, 64.1 (2C), 68.4, 68.5, 100.8, 105.4, 119.4, 132.1, 159.0, 161.9

Example 2

Synthesis of TIPS3-OMP-Type Protecting Agent

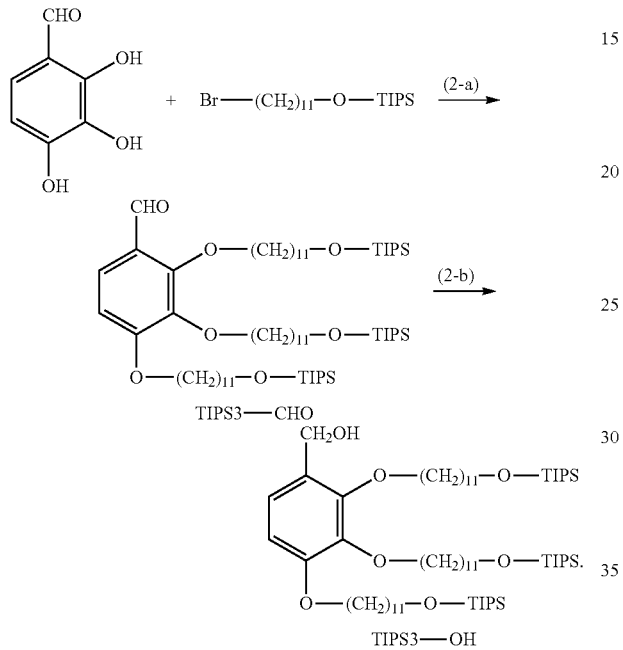

(Hereinafter, TIPS3-CHO and TIPS3-OH indicate the respective structures in the formula.)

Example (2-a): TIPS3-CHO

Br—(CH$_2$)$_{11}$—O-TIPS (4.64 g, 11.38 mmol), 2,3,4-trihydroxybenzaldehyde (0.50 g, 3.25 mmol), and potassium carbonate (2.25 g, 16.25 mmol) were suspended in DMF (21.7 mL), and the suspension was heated to 85° C. and was stirred for 4 hours. The reaction solution was filtered, and the residue was washed with heptane (45.5 mL). The heptane layer was separated from the filtrate, and heptane (21.7 mL) was added to the layer, followed by liquid-liquid extraction with DMF (21.7 mL). The liquid-liquid extraction with heptane and DMF was further repeated once. Heptane (21.7 mL) was added to the resulting heptane layer, followed by liquid-liquid extraction with 1 N hydrochloric acid (21.7 mL) once, a 5% sodium bicarbonate aqueous solution (21.7 mL) once, and water (21.7 mL) once. Heptane (21.7 mL) was added to the resulting heptane layer, followed by liquid-liquid extraction with DMF (21.7 mL). Heptane (21.7 mL) was added to the resulting heptane layer, followed by liquid-liquid extraction with acetonitrile (21.7 mL). The solvent was distilled to obtain TIPS3-CHO (3.97 g, yield: quant.).

$^1$H-NMR (400 MHz, CDCl$_3$) δ 1.03-1.08 (m, 63H), 1.20-1.39 (m, 42H), 1.41-1.57 (m, 6H), 1.72-1.89 (m, 6H), 3.63-3.69 (m, 6H), 3.97 (t, 2H), 4.04 (t, 2H), 4.17 (t, 2H), 6.72 (d, 1H), 7.58 (d, 1H), 10.26 (s, 1H)

Example (2-b)

TIPS3-CHO (2.95 g, 2.60 mmol) was dissolved in a mixed solution of THF (anhydrous, 19.8 mL) and methanol (0.99 mL). The solution was cooled to 5° C., and sodium borohydride (0.12 g, 3.12 mmol) was added thereto, followed by stirring for 1 hour. The reaction was quenched with 1 N hydrochloric acid (2.5 mL), and CPME (73.8 mL) was added thereto, followed by liquid-liquid extraction with 1 N hydrochloric acid (22.1 mL) three times, a 5% sodium bicarbonate aqueous solution (22.1 mL) once, and water (22.1 mL) once. The solvent was distilled. The resulting residue was dissolved in heptane (73.8 mL), followed by liquid-liquid extraction with DMF (36.9 mL). Heptane (36.9 mL) was added to the resulting heptane layer, followed by liquid-liquid extraction with acetonitrile (36.9 mL). The liquid-liquid extraction with heptane and acetonitrile was further repeated once. The solvent was then distilled, and the resulting residue was purified by silica gel column chromatography (hexane:ethyl acetate=50:1→20:1→12:1) to obtain TIPS3-OH (2.57 g, yield: 87.0%, two steps).

$^1$H-NMR (400 MHz, CDCl$_3$) δ 1.03-1.07 (m, 63H), 1.20-1.39 (m, 42H), 1.40-1.57 (m, 6H), 1.71-1.86 (m, 6H), 2.17 (t, 1H), 3.63-3.69 (m, 6H), 3.88-3.98 (m, 4H), 4.10 (t, 2H), 4.60 (d, 2H), 6.60 (d, 1H), 6.92 (d, 1H)

$^{13}$C-NMR (100 MHz, CDCl$_3$) δ 12.2 (9C), 18.2 (18C), 26.0 (3C), 26.2, 26.3 (2C), 29.5-30.7 (18C), 33.2 (3C), 62.2, 63.7 (3C), 68.9, 73.7, 74.2, 108.0, 123.2, 127.0, 141.7, 151.6, 153.6

ESIMS MH+ 1,158.2

Example 3

Synthesis of TIPS6-OP-Type Protecting Agent

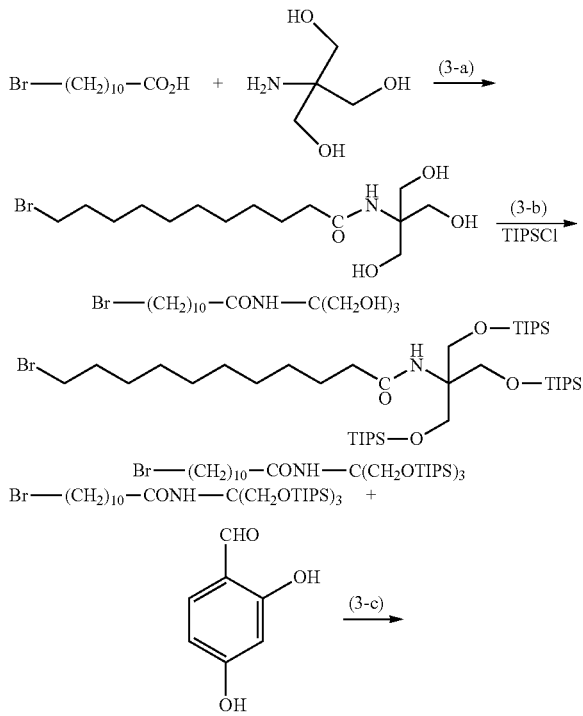

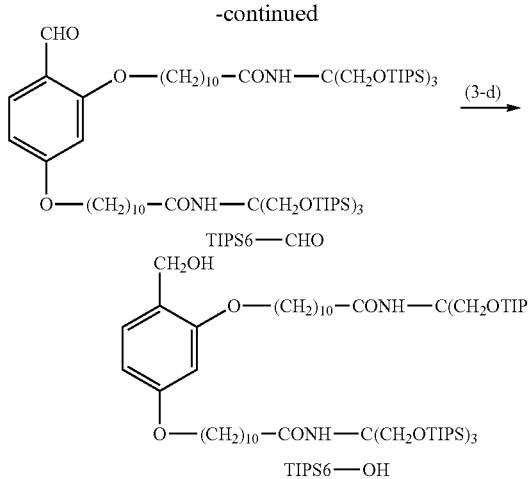

(Hereinafter, Br—(CH$_2$)$_{10}$—CONH—C(CH$_2$OH)$_3$, Br—(CH$_2$)$_{10}$—CONH—C(CH$_2$OH)$_3$, TIPS6-CHO, and TIPS6-OH indicate the respective structures in the formula.)

Example (3-a)

11-Bromoundecanoic acid (1.00 g, 3.77 mmol) and trihydroxymethylaminomethane (0.69 g, 5.66 mmol) were suspended in DMF (37.7 mL). DMT-MM (3.13 g, 11.31 mmol) and DIPEA (2.6 mL, 15.08 mmol) were added thereto, followed by stirring at room temperature for 1 hour. Ethyl acetate (189 mL) was added to the reaction solution, followed by washing with a saturated sodium bicarbonate aqueous solution (94 mL) once and 20% sodium chloride aqueous solution (94.3 mL) three times to remove the aqueous phase. Anhydrous magnesium sulfate was added to the organic phase, and the mixture was thoroughly stirred, followed by filtration. The filtrate was concentrated under reduced pressure to distill the solvent. A mixture containing Br—(CH$_2$)$_{10}$—CONH—C(CH$_2$OH)$_3$ was thus obtained.

Example (3-b)

The mixture obtained in the step (a) was dissolved in DMF (40.7 mL). Imidazole (2.56 g, 37.63 mmol) was added to the solution, and TIPSCl (3.9 mL, 18.25 mmol) was dropwise added thereto. The mixture was then heated to 85° C. and was stirred for 1 hour. Ethyl acetate (200 mL) was added to the reaction solution, followed by washing with 1 N hydrochloric acid (100 mL) once, a saturated sodium bicarbonate aqueous solution (100 mL) once, and 20% sodium chloride aqueous solution (100 mL) twice to remove the aqueous phase. Anhydrous magnesium sulfate was added to the organic phase, and the mixture was thoroughly stirred, followed by filtration. The filtrate was concentrated under reduced pressure to distill the solvent. The resulting residue was purified by silica gel column chromatography (hexane:ethyl acetate=75:1) to obtain Br—(CH$_2$)$_{10}$—CONH—C(CH$_2$OTIPS)$_3$ (2.23 g, yield: 70.6%, two steps).

$^1$H-NMR (400 MHz, CDCl$_3$) δ 0.93-1.10 (m, 63H), 1.21-1.30 (m, 10H), 1.37-1.43 (m, 2H), 1.51-1.59 (m, 2H), 1.72-1.79 (m, 2H), 2.07 (t, 2H), 3.52 (t, 2H), 4.01-4.03 (m, 6H), 5.71 (s, 1H)

$^{13}$C-NMR (100 MHz, CDCl$_3$) δ 12.6 (9C), 18.1 (18C), 25.8, 27.0, 29.0-29.5 (6C), 32.7, 37.8, 45.2, 61.3 (2C), 62.1, 172.5

ESIMS MH+ 836.5

Example (3-c): TIPS6-CHO

Br—(CH$_2$)$_{10}$—CONH—C(CH$_2$OTIPS)$_3$ (1.02 g, 1.22 mmol), 2,4-dihydroxybenzaldehyde (70 mg, 0.51 mmol), and potassium carbonate (0.25 g, 1.82 mmol) were suspended in DMF (5.1 mL), and the suspension was heated to 100° C. and was stirred for 8 hours. The reaction solution was filtered, and the residue was washed with heptane (10.6 mL). The heptane layer was separated from the filtrate, and heptane (5.1 mL) was added to the layer, followed by liquid-liquid extraction with DMF (5.1 mL). The liquid-liquid extraction with heptane and DMF was further repeated once. Heptane (5.1 mL) was added to the resulting heptane layer, followed by liquid-liquid extraction with 1 N hydrochloric acid (5.1 mL) once, a 5% sodium bicarbonate aqueous solution (5.1 mL) once, and water (5.1 mL) once. Heptane (5.1 mL) was added to the resulting heptane layer, followed by liquid-liquid extraction with DMF (5.1 mL). Heptane (5.1 mL) was added to the resulting heptane layer, followed by liquid-liquid extraction with acetonitrile (5.1 mL). The solvent was distilled, and the residue was purified by silica gel column chromatography (hexane:ethyl acetate=125:1) to obtain TIPS6-CHO (0.48 g, yield: 57.6%).

$^1$H-NMR (400 MHz, CDCl$_3$) δ 0.90-1.11 (m, 126H), 1.20-1.46 (m, 24H), 1.53-1.60 (m, 4H), 1.72-1.83 (m, 4H), 2.08 (t, 4H), 4.01-4.03 (m, 16H), 5.71-5.74 (m, 2H), 6.40 (d, 1H), 6.48-6.51 (m, 1H), 7.78 (d, 1H), 10.31 (s, 1H)

$^{13}$C-NMR (100 MHz, CDCl$_3$) δ 12.1 (18C), 18.1 (36C), 25.9 (2C), 26.1, 26.2, 29.2-29.7 (12C), 37.9 (2C), 61.3 (6C), 62.2 (2C), 68.4, 68.5, 99.1, 106.3, 119.1, 130.3, 163.5, 165.9, 172.6 (2C), 188.5

ESIMS MH+ 1,650.7

Example (3-d): TIPS6-OH

TIPS6-CHO (0.44 g, 0.27 mmol) was dissolved in a mixed solution of THF (anhydrous, 2.0 mL) and methanol (0.10 mL). The solution was cooled to 5° C., and sodium borohydride (12 mg, 0.32 mmol) was added thereto, followed by stirring at room temperature for 1 hour. The reaction was quenched with 1 N hydrochloric acid, and CPME (11.0 mL) was added thereto, followed by washing with 1 N hydrochloric acid (3.3 mL) three times, a 5% sodium bicarbonate aqueous solution (3.3 mL) once, and water (3.3 mL) once to remove the aqueous phase. The resulting residue was dissolved in heptane (11.0 mL), followed by liquid-liquid extraction with DMF (5.5 mL). Heptane (5.5 mL) was added to the resulting heptane layer, followed by liquid-liquid extraction with acetonitrile (5.5 mL). The liquid-liquid extraction with heptane and acetonitrile was further repeated once, and the solvent was then distilled to obtain TIPS6-OH (0.22 g, yield: 50.1%).

$^1$H-NMR (400 MHz, CDCl$_3$) δ 0.93-1.10 (m, 126H), 1.22-1.42 (m, 24H), 1.52-1.57 (m, 4H), 1.71-1.80 (m, 4H), 2.08 (t, 4H), 3.26 (s, 1H), 3.90-4.03 (m, 16H), 4.60 (d, 2H), 5.71-5.74 (m, 2H), 6.39-6.44 (m, 2H), 7.12 (d, 1H)

$^{13}$C-NMR (100 MHz, CDCl$_3$) δ 12.0 (18C), 18.1 (36C), 25.7 (2C), 26.1, 26.2, 29.3-29.6 (12C), 37.7 (2C), 61.2, 61.3 (6C), 62.0, 62.1, 68.1, 68.3, 99.8, 104.4, 121.9, 129.5, 158.0, 160.2, 172.5 (2C)

ESIMS MH+ 1,652.7

Example 4

Synthesis of TIPS9-OMP-Type Protective Agent

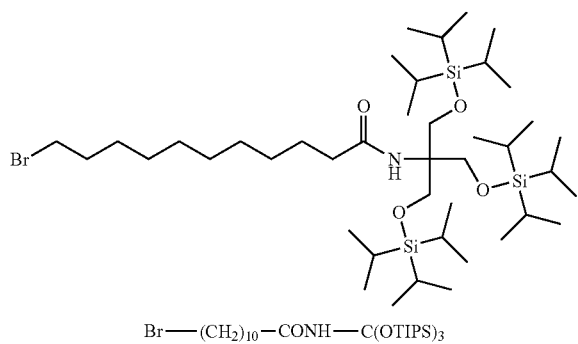

Br—(CH$_2$)$_{10}$—CONH—C(OTIPS)$_3$

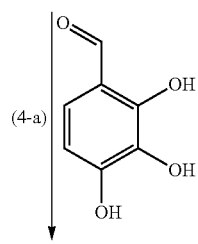

(4-a)

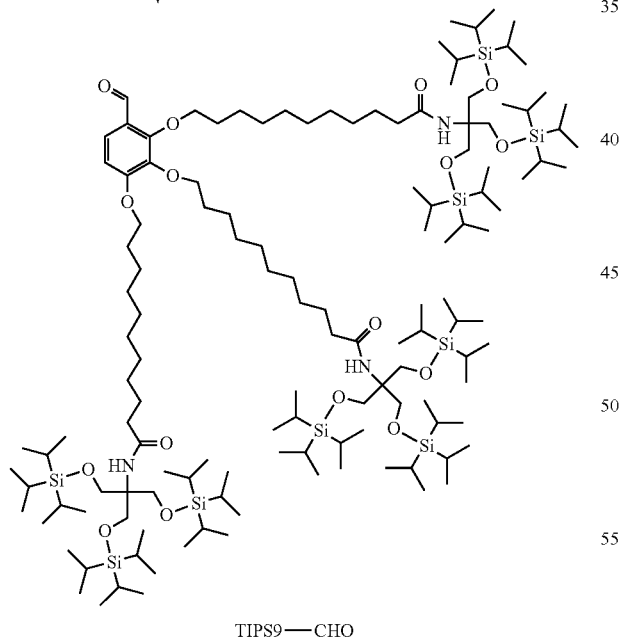

TIPS9—CHO (Hereinafter, TIPS9-CHO indicates the structure in the formula.)

Example (4-a): TIPS9-CHO

Br—(CH$_2$)$_{10}$—CONH—C(CH$_2$OTIPS)$_3$ (0.91 g, 1.09 mmol), 2,3,4-trihydroxybenzaldehyde (50 mg, 0.32 mmol), and potassium carbonate (0.22 g, 1.62 mmol) were suspended in DMF (3.2 mL). The suspension was heated to 100° C. and stirred for 2 hours and was then heated to 120° C. and stirred for 8.5 hours. The reaction solution was filtered, and the filter residue was washed with heptane (6.8 mL). The heptane layer was separated from the filtrate, and heptane (3.2 mL) was added to the layer, followed by liquid-liquid separation with DMF (3.2 mL). The liquid-liquid separation with heptane and DMF was further repeated once. Heptane (3.2 mL) was added to the resulting heptane layer, followed by liquid-liquid extraction with 1 N hydrochloric acid (3.2 mL) once, a 5% sodium bicarbonate aqueous solution (3.2 mL) once, and water (3.2 mL) once. Heptane (3.2 mL) was added to the resulting heptane layer, followed by liquid-liquid extraction with acetonitrile (3.2 mL). The liquid-liquid extraction with heptane and acetonitrile was further repeated twice. The solvent was distilled, and the resulting residue was purified by silica gel column chromatography (heptane:ethyl acetate=20:1→12:1) to obtain TIPS9-CHO (0.38 g, yield: 47.9%).

$^1$H-NMR (400 MHz, CDCl$_3$) δ 1.02-1.08 (m, 189H), 1.23-1.51 (m, 36H), 1.52-1.59 (m, 6H), 1.71-1.89 (m, 6H), 2.08 (t, 6H), 3.94-4.06 (m, 22H), 4.16 (t, 2H), 5.71-5.81 (m, 3H), 6.71 (d, 1H), 7.57 (d, 1H), 10.26 (s, 1H)

$^{13}$C-NMR (100 MHz, CDCl$_3$) δ 12.1 (27C), 18.1 (54C), 26.0 (3C), 26.1, 26.2 (2C), 29.3-30.4 (18C), 37.9 (3C), 61.3 (9C), 62.2 (3C), 69.1, 73.9, 75.4, 108.2, 123.6, 123.8, 141.2, 156.8, 159.3, 172.6 (3C), 189.3

Example (4-b): TIPS9-OH

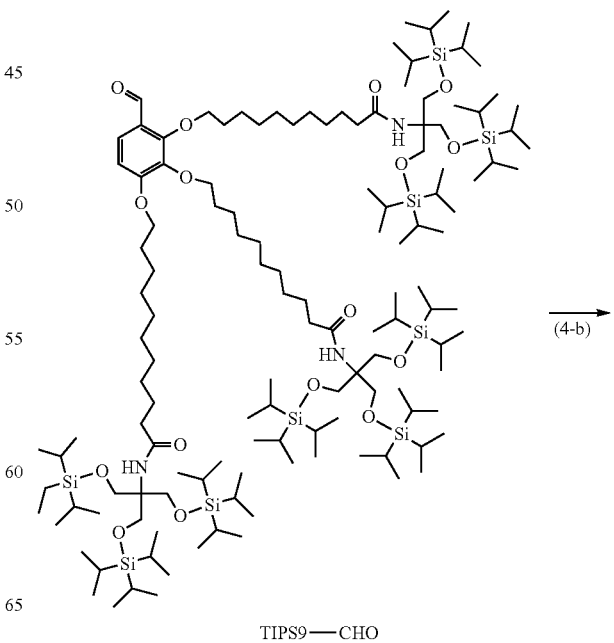

TIPS9—CHO

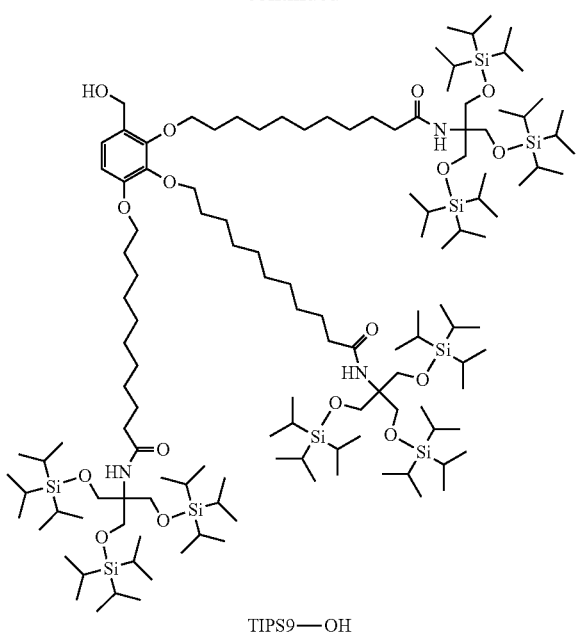

TIPS9—OH (Hereinafter, TIPS9-OH indicates the structure in the formula.)

TIPS9-CHO (0.17 g, 0.069 mmol) was dissolved in a mixed solution of THP (anhydrous, 0.53 mL) and methanol (0.026 mL), and sodium borohydride (3.1 mg, 0.083 mmol) was added to the solution, followed by stirring for 1 hour. The reaction was quenched with 1 N hydrochloric acid (0.066 mL), and CPME (4.2 mL) was added thereto, followed by washing with 1 N hydrochloric acid (1.3 mL) once, a 5% sodium bicarbonate aqueous solution (1.3 mL) once, and water (1.3 mL) once. The solvent was distilled, and the resulting residue was dissolved in heptane (4.2 mL), followed by liquid-liquid extraction with DMF (2.1 mL). Heptane (2.1 mL) was added to the resulting heptane layer, followed by liquid-liquid extraction with acetonitrile (2.1 mL). The liquid-liquid extraction with heptane and acetonitrile was further repeated once, and the solvent was then distilled to obtain TIPS9-OH (0.15 g, yield: 89.2%).

$^1$H-NMR (400 MHz, CDCl$_3$) δ 1.02-1.08 (m, 189H), 1.23-1.51 (m, 36H), 1.51-1.62 (m, 6H), 1.70-1.85 (m, 6H), 2.04-2.16 (m, 7H), 3.96-4.00 (t, 2H), 4.00-4.13 (m, 22H), 4.60 (s, 2H), 5.71-5.80 (m, 3H), 6.59 (d, 1H), 6.92 (d, 1H)

$^{13}$C-NMR (100 MHz, CDCl$_3$) δ 12.1 (27C), 18.1 (54C), 26.0 (3C), 26.2 (2C), 26.3, 29.4-30.7 (18C), 37.9 (3C), 61.4 (9C), 62.1, 62.2 (3C), 68.9, 73.7, 74.1, 108.1, 123.2, 127.0, 141.7, 151.6, 153.5, 172.6 (3C)

Example 5

Synthesis of TBDPS2-OP-Type Protecting Agent

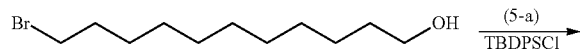

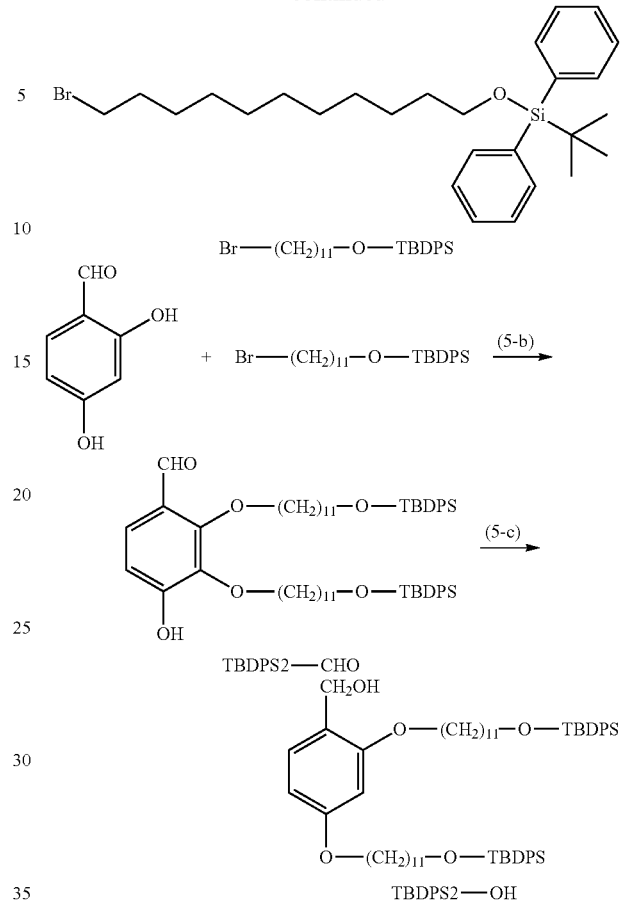

(Hereinafter, Br—(CH$_2$)$_{11}$—O-TBDPS, TBDPS2-CHO, and TBDPS2-OH indicate the respective structures in the formula.)

Example (5-a)

1-Bromoundecanol (4.00 g, 15.9 mmol) was dissolved in dichloromethane (15.9 mL), and imidazole (2.39 g, 35.0 mmol) was added to the solution. The mixture was cooled to 5° C., and TBDPSCl (4.47 mL, 17.5 mmol) was dropwise added thereto. The mixture was warmed to room temperature and was stirred for 30 minutes. CPME (63.7 mL) was added to the reaction solution, followed by washing with water (15.9 mL) once, 1 N hydrochloric acid (15.9 mL) once, and water (15.9 mL) twice. The solvent was distilled. The residue was dissolved in heptane (61.7 mL), followed by liquid-liquid extraction with DMF (31.8 mL). Heptane (15.9 mL) was added to the resulting heptane layer, followed by liquid-liquid extraction with acetonitrile (31.8 mL). The liquid-liquid extraction with heptane and acetonitrile was further repeated once, and the solvent was then distilled to obtain Br—(CH$_2$)$_{11}$—O-TBDPS (6.62 g, yield: 84.9%).

$^1$H-NMR (400 MHz, CDCl$_3$) δ 1.06 (s, 9H), 1.24-1.48 (m, 14H), 1.57 (quin., 2H), 1.86 (quin., 2H), 3.41 (t, 2H), 3.67 (t, 2H), 7.35-7.46 (m, 6H), 7.66-7.70 (m, 4H)

$^{13}$C-NMR (100 MHz, CDCl$_3$) δ 19.4, 25.9, 27.0 (3C), 28.3, 28.9, 29.5, 29.6 (2C), 29.7, 32.7, 33.0, 34.2, 64.2, 127.7 (4C), 129.6 (2C), 134.3 (2C), 135.7 (4C)

ESIMS MNa+ 511.3

Example (5-b): TBDPS2-CHO

Br—(CH$_2$)$_{11}$—O-TBDPS (3.34 g, 6.89 mmol), 2,4-dihydroxybenzaldehyde (0.42 g, 3.06 mmol), and potassium carbonate (1.52 g, 11.0 mmol) were suspended in DMF (20.4 mL). The suspension was heated to 85° C. and was stirred for 2 hours. The reaction solution was filtered, and the residue was washed with heptane (42.9 mL). The heptane layer was separated from the filtrate, and heptane (20.4 mL) was added to the layer, followed by liquid-liquid extraction with DMF (20.4 mL). Heptane (20.4 mL) was added to the resulting heptane layer, followed by liquid-liquid extraction with 1 N hydrochloric acid (20.4 mL) once, a 5% sodium bicarbonate aqueous solution (20.4 mL) once, and water (20.4 mL) once. Heptane (20.4 mL) was added to the resulting heptane layer, followed by liquid-liquid extraction with acetonitrile (20.4 mL). Heptane (20.4 mL) was added to the resulting heptane layer, followed by liquid-liquid extraction with acetonitrile (20.4 mL). The solvent was distilled, and the resulting residue was purified by silica gel column chromatography (hexane:ethyl acetate=82:1) to obtain TBDPS2-CHO (0.62 g, 21.2%).

$^1$H-NMR (400 MHz, CDCl$_3$) δ 1.06 (s, 18H), 1.20-1.39 (m, 24H), 1.41-1.61 (m, 8H), 1.74-1.89 (m, 4H), 3.66 (t, 4H), 3.96-4.06 (m, 4H), 6.43 (d, 1H), 6.48-6.54 (m, 1H), 7.28-7.45 (m, 12H), 7.61-7.70 (m, 8H), 7.81 (d, 1H), 10.34 (s, 1H)

$^{13}$C-NMR (100 MHz, CDCl$_3$) δ 19.4 (2C), 25.9 (2C), 26.1, 26.2, 27.0 (6C), 29.2-29.7 (12C), 32.7 (2C) 64.1 (2C), 68.6 (2C), 99.1, 106.3, 119.1, 127.7 (8C), 129.6 (4C), 130.3, 134.3 (4C), 135.7 (8C), 163.5, 165.9, 188.5

ESIMS MNa+ 977.7

Example (5-c): TBDPS2-OH

TBDPS2-CHO (0.15 g, 0.16 mmol) was dissolved in a mixed solution of THP (anhydrous, 1.2 mL) and methanol (61 μL), and sodium borohydride (7.2 mg, 0.19 mmol) was added to the solution, followed by stirring for 1 hour. The reaction solution was cooled to 5° C., and 1 N hydrochloric acid (0.15 mL) was then added thereto to quench the reaction. CPME (3.8 mL) was added to the solution, followed by liquid-liquid extraction with 1 N hydrochloric acid (1.1 mL) three times, a 5% sodium bicarbonate aqueous solution (1.1 mL) once, and water (1.1 mL) once. Anhydrous sodium sulfate was added to the resulting organic phase. The mixture was thoroughly stirred and was then filtered. The filtrate was concentrated under reduced pressure to distill the solvent. The resulting residue was dissolved in heptane (1.5 mL), and the mixture was then concentrated under reduced pressure to distill the solvent to obtain TBDPS2-OH (0.15 g, yield: quant).

$^1$H-NMR (400 MHz, CDCl$_3$) δ 1.05 (s, 18H), 1.20-1.39 (m, 24H), 1.41-1.60 (m, 8H), 1.71-1.89 (m, 4H), 2.21 (s, 1H), 3.65 (t, 4H), 3.88-4.01 (m, 4H), 4.61 (s, 2H), 6.38-6.44 (m, 1H), 6.46 (d, 1H), 7.13 (d, 1H), 7.28-7.44 (m, 12H), 7.61-7.70 (m, 8H)

$^{13}$C-NMR (100 MHz, CDCl$_3$) δ 19.4 (2C), 25.9 (2C), 26.2, 26.3, 27.0 (6C), 29.4-29.8 (12C), 32.7 (2C) 62.2, 64.2 (2C), 68.2, 68.3, 100.0, 104.6, 121.8, 127.7 (8C), 129.6 (4C), 129.7, 134.4 (4C), 135.7 (8C), 158.3, 160.3

ESIMS MNa+ 979.7

Example 6

Synthesis of TIPS2-OH(C$_8$)

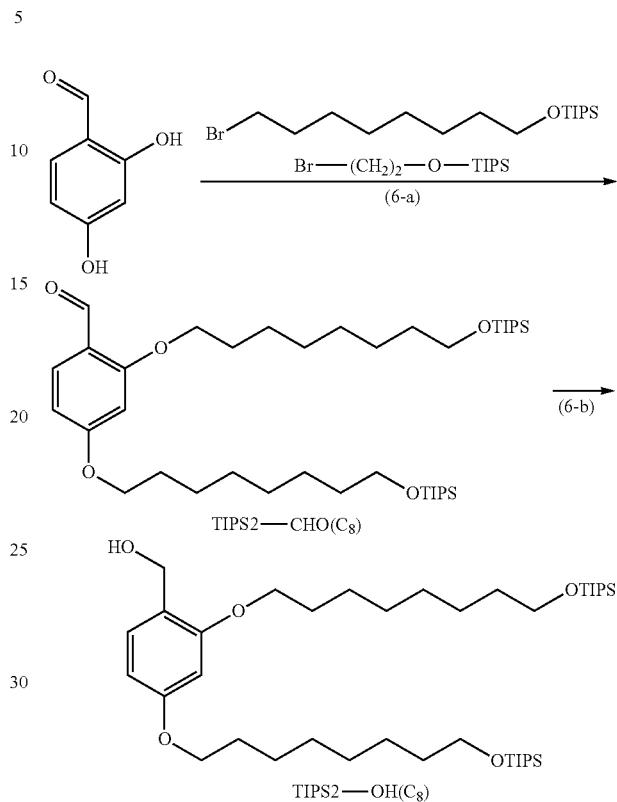

(Hereinafter, Br—(CH$_2$)$_8$—O-TIPS, TIPS2-CHO(Ca), and TIPS2-OH(C$_8$) indicate the respective structures in the formula.)

Example (6-a): TIPS2-CHO(C$_8$)

Br—(CH$_2$)$_8$—O-TIPS (1.78 g, 4.87 mmol), 2,4-dihydroxybenzaldehyde (0.30 g, 2.16 mmol), and potassium carbonate (1.08 g, 7.79 mmol) were suspended in DMF (14.4 mL). The suspension was heated to 85° C. and was stirred for 2 hours. The reaction solution was filtered, and the residue was washed with heptane (30.3 mL). The heptane layer was separated from the filtrate, and heptane (4.4 mL) was added to the layer, followed by liquid-liquid extraction with acetonitrile (14.4 mL). Heptane (14.4 mL) was added to the resulting heptane layer, followed by liquid-liquid extraction with 1 N hydrochloric acid. (14.4 mL) once, a 5% sodium bicarbonate aqueous solution (14.4 mL) once, and water (14.4 mL) once. Heptane (14.4 mL) was added to the resulting heptane layer, followed by liquid-liquid extraction with acetonitrile (14.4 mL). The liquid-liquid extraction with heptane and acetonitrile was further repeated once, and the heptane layer was concentrated under reduced pressure. The resulting residue was purified by silica gel column chromatography (hexane:ethyl acetate=75:1) to obtain TIPS2-CHO(Ca) (1.29 g, yield: 84.6%).

$^1$H-NMR (400 MHz, CDCl$_3$) δ 1.04-1.09 (m, 42H), 1.32-1.40 (m, 12H), 1.43-1.51 (m, 4H), 1.51-1.59 (m, 4H), 1.75-1.88 (m, 4H), 3.67 (t, 4H), 3.98-4.05 (m, 4H), 6.41 (d, 1H), 6.51 (dd, 1H), 7.79 (d, 1H), 10.32 (s, 1H)

$^{13}$C-NMR (100 MHz, CDCl$_3$) δ 12.2 (6C), 18.2 (12C), 25.9 (2C), 26.1, 26.2, 29.2 (2C), 29.5 (4C), 33.1 (2C), 63.6 (2C), 68.5, 68.6, 99.1, 106.3, 119.1, 130.3, 163.5, 165.9, 188.5

ESIMS MH+ 707.3

Example (6-b): TIPS2-OH(C$_8$)

TIPS2-CHO(C$_8$) (1.04 g, 1.47 mmol) was dissolved in a mixed solution of THF (anhydrous, 11.2 mL) and methanol (0.56 mL), and sodium borohydride (67 mg, 1.76 mmol) was added to the solution, followed by stirring at room temperature for 1 hour. The reaction solution was cooled to 5° C., and 1 N hydrochloric acid (1.40 mL) was then added thereto to quench the reaction. CPME (26.0 mL) was added to the solution, followed by liquid-liquid extraction with 1 N hydrochloric acid (7.8 mL) three times, a 5% sodium bicarbonate aqueous solution (7.8 mL) once, and water (7.8 mL) once. The resulting organic layer was concentrated under reduced pressure. The residue was dissolved in heptane (20.8 mL), followed by liquid-liquid extraction with acetonitrile (10.4 mL). The liquid-liquid extraction with heptane and acetonitrile was further repeated once, and heptane layer was then concentrated under reduced pressure to obtain TIPS2-OH(C$_8$) (1.00 g).

$^1$H-NMR (400 MHz, CDCl$_3$) δ 1.04-1.08 (m, 42H), 1.32-1.40 (m, 12H), 1.42-1.50 (m, 4H), 1.51-1.59 (m, 4H), 1.72-1.87 (m, 4H), 2.23 (br, 1H), 3.67 (t, 4H), 3.93 (t, 2H), 3.98 (t, 2H), 4.61 (s, 2H), 6.42 (dd, 1H), 6.45 (d, 1H), 7.13 (d, 1H)

$^{13}$C-NMR (100 MHz, CDCl$_3$) δ 12.2 (6C), 18.2 (12C), 25.9 (2C), 26.2, 26.3, 29.4 (2C), 29.5-29.6 (4C), 33.2 (2C), 62.2, 63.6 (2C), 68.2, 68.3, 99.9, 104.6, 121.9, 129.7, 158.3, 160.3

ESIMS MNa+ 731.4

Example 7

Synthesis of TIPS2-OH(C$_{14}$)

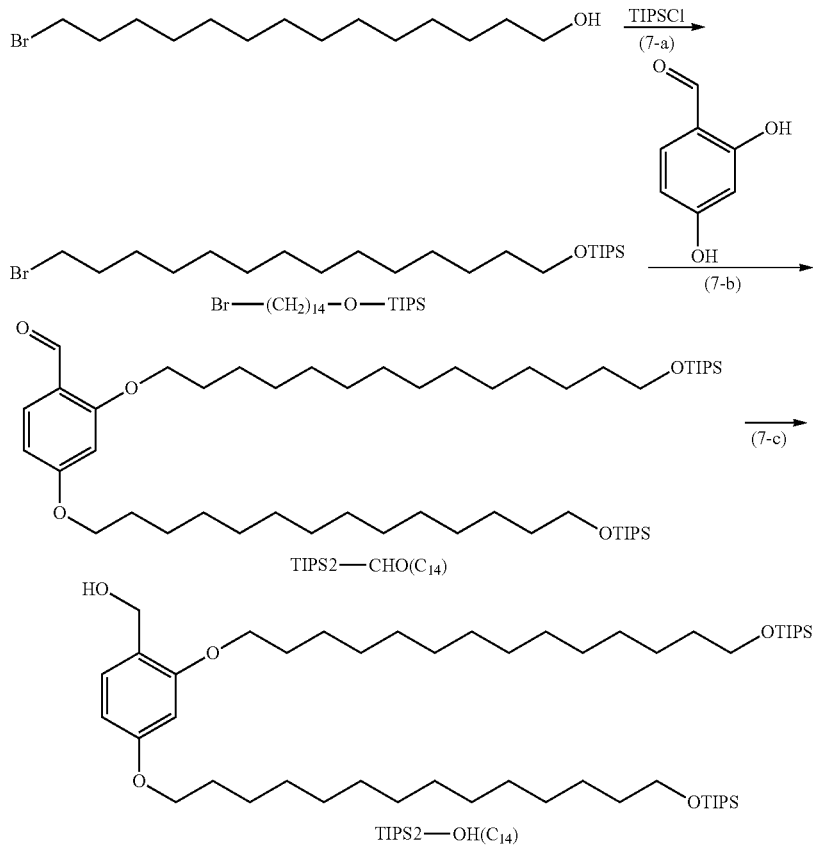

(Hereinafter, Br—(CH$_2$)$_{14}$—O-TIPS, TIPS2-CHO(C$_{14}$), and TIPS2-OH(C$_{14}$) indicate the respective structures in the formula.)

Example (7-a)

14-Bromo-1-tetradecanol (10.00 g, 34.1 mmol) was dissolved in dichloromethane (34.1 mL), and imidazole (5.11 g, 75.0 mmol) was added to the solution. TIPSCl (7.95 mL, 37.5 mmol) was dropwise added to the mixture, followed by stirring at room temperature for 3 hours. The reaction solution was concentrated under reduced pressure, and the resulting residue was dissolved in heptane (136 mL), followed by liquid-liquid extraction with water (34 mL) once, 1 N hydrochloric acid (34 mL) once, water (34 mL) twice, and acetonitrile (34 mL) once. Heptane (34 mL) was added to the resulting heptane layer, followed by liquid-liquid extraction with acetonitrile (34 mL). The liquid-liquid extraction with heptane and acetonitrile was further repeated once, and the heptane layer was then concentrated under reduced pressure to obtain Br—(CH$_2$)$_{14}$—O-TIPS (15.41 g).

$^1$H-NMR (400 MHz, CDCl$_3$) δ 1.04-1.08 (m, 21H), 1.24-1.38 (m, 18H), 1.42 (quin., 2H), 1.53 (quin., 2H), 1.85 (quin., 2H), 3.40 (t, 2H), 3.67 (t, 2H)

Example (7-b): TIPS2-CHO(C$_{14}$)

Br—(CH$_2$)$_{14}$—O-TIPS (1.74 g, 3.87 mmol), 2,4-dihydroxybenzaldehyde (0.24 g, 1.72 mmol), and potassium carbonate (0.86 g, 6.19 mmol) were suspended in DMF (11.5 mL), and the suspension was heated to 85° C. and was stirred for 2 hours. The reaction solution was filtered, and the residue was washed with heptane (24.1 mL). The heptane layer was separated from the filtrate, and heptane (11.5 mL) was added to the layer, followed by liquid-liquid extraction with DMF (11.5 mL). Heptane (11.5 mL) was added to the resulting heptane layer, followed by liquid-liquid extraction with 1 N hydrochloric acid (11.5 mL) once, a 5% sodium bicarbonate aqueous solution (11.5 mL) once, and water (11.5 mL) once. Heptane (11.5 mL) was added to the resulting heptane layer, followed by liquid-liquid extraction with acetonitrile (11.5 mL). The liquid-liquid extraction with heptane and acetonitrile was further repeated once, and the heptane layer was concentrated under reduced pressure. The resulting residue was purified by silica gel column chromatography (hexane:ethyl acetate=100:0→0:100) to obtain TIPS2-CHO(C$_{14}$) (1.22 g, yield: 80.9%).

$^1$H-NMR (400 MHz, CDCl$_3$) δ 1.04-1.08 (m, 42H), 1.24-1.40 (m, 36H), 1.40-1.59 (m, 8H), 1.75-1.88 (m, 4H), 3.66 (t, 4H), 3.98-4.05 (m, 4H), 6.42 (d, 1H), 6.51 (dd, 1H), 7.79 (d, 1H), 10.33 (s, 1H)

$^{13}$C-NMR (100 MHz, CDCl$_3$) δ 12.2 (6C), 18.2 (12C), 26.0 (2C), 26.1, 26.2, 29.2-29.8 (18C), 33.2 (2C), 63.7 (2C), 68.6 (2C), 99.1, 106.3, 119.1, 130.3, 163.5, 165.9, 188.5

ESIMS MNa+ 897.7

Example (7-c): TIPS2-OH(C$_{14}$)

TIPS2-CHO(C$_{14}$) (0.28 g, 0.32 mmol) was dissolved in a mixed solution of THF (anhydrous, 2.45 mL) and methanol (0.12 mL), and sodium borohydride (15 mg, 0.39 mmol) was added to the solution, followed by stirring at room temperature for 1 hour. The reaction solution was cooled to 5° C., and 1 N hydrochloric acid (0.31 mL) was added thereto to quench the reaction. CPME (7.0 mL) was added to the solution, followed by liquid-liquid extraction with 1 N hydrochloric acid (2.1 mL) three times, a 5% sodium bicarbonate aqueous solution (2.1 mL) once, and water (2.1 mL) once. Anhydrous sodium sulfate was added to the organic layer, and the mixture was thoroughly stirred and was then filtered. The filtrate was concentrated under reduced pressure to obtain TIPS2-OH(C$_{14}$) (0.27 g).

$^1$H-NMR (400 MHz, CDCl$_3$) δ 1.04-1.08 (m, 42H), 1.24-1.40 (m, 36H), 1.40-1.50 (m, 4H), 1.50-1.58 (m, 4H), 1.72-1.85 (m, 4H), 2.23 (br, 1H), 3.67 (t, 4H), 3.91-4.01 (m, 4H), 4.61 (s, 2H), 6.42 (dd, 1H), 6.45 (d, 1H), 7.13 (d, 1H)

$^{13}$C-NMR (100 MHz, CDCl$_3$) δ 12.2 (6C), 18.2 (12C), 26.0 (2C), 26.2, 26.3, 29.4-29.8 (18C), 33.2 (2C), 62.2, 63.7 (2C), 68.2, 68.3, 99.9, 104.6, 121.9, 129.7, 158.3, 160.3

ESIMS MNa+ 899.7

Example 8

Synthesis of TIPS2-NOH(C$_{14}$)

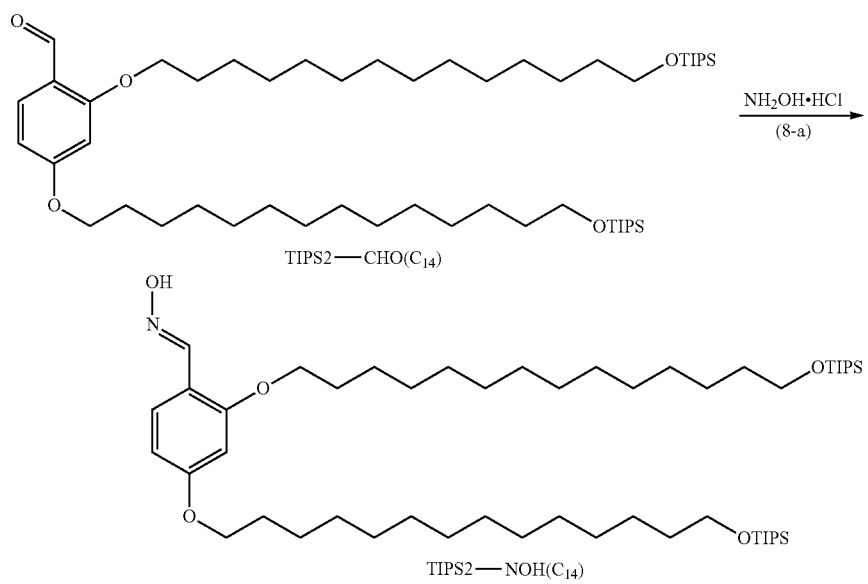

(Hereinafter, TIPS2-NOH(C$_{14}$) indicates the structure in the formula.)

Example (8-a): TIPS2-NOH(C$_{14}$)

TIPS2-CHO(C$_{14}$) (0.22 g, 0.25 mmol) was dissolved in dichloromethane (1.2 mL), and hydroxylamine hydrochloride (53 mg, 0.76 mmol) was added to the solution. The mixture was cooled to 5° C., and triethylamine (177 ML, 1.27 mmol) was added thereto. The mixture was warmed to room temperature and stirred for 23 hours. The reaction solution was cooled to 5° C., and the reaction was quenched with 1 N hydrochloric acid (0.51 mL). Heptane (6.7 mL) was added thereto, followed by liquid-liquid extraction with 1 N hydrochloric acid (3.3 mL) three times, a 5% sodium bicarbonate aqueous solution (3.3 mL) three times, and water (3.3 mL) once. Heptane (3.3 mL) was added to the resulting heptane layer, followed by liquid-liquid extraction with acetonitrile (3.3 mL). The liquid-liquid extraction with heptane and acetonitrile was further repeated once, and the heptane layer was concentrated under reduced pressure to obtain TIPS2-NOH(C$_{14}$) (0.17 g).

ESIMS MH+ 890.8

Example 9

Synthesis of TIPS2-NH(CH$_2$)$_2$CH$_3$ (C$_{14}$)

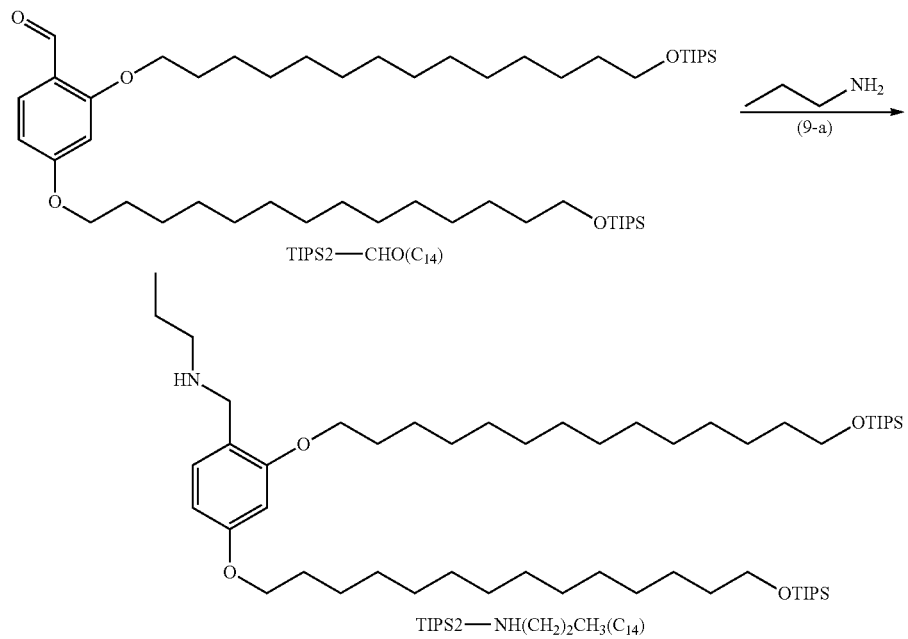

(Hereinafter, TIPS2-NH(CH$_2$)$_2$CH$_3$ (C$_{14}$) indicates the structure in the formula.)

Example (9-a): TIPS2-NH(CH$_2$)$_2$CH$_3$(C$_{14}$)       40

TIPS2-CHO(C$_{14}$) (0.30 g, 0.34 mmol) was dissolved in THF (anhydrous, 0.35 mL). Propylamine (40 μL, 0.48 mmol), acetic acid (124 μL, 2.17 mmol), and 2-picoline borane (63 mg, 0.59 mmol) were added to the solution, followed by stirring at room temperature for 1 hour and 45 minutes. The reaction solution was cooled to 5° C., and the reaction was quenched with 1 N hydrochloric acid (0.24 mL). CPME (12.1 mL) was added thereto, followed by liquid-liquid extraction with 1 N hydrochloric acid (3.6 mL) once, a 5% sodium bicarbonate aqueous solution (3.6 mL) twice, and water (3.6 mL) once. The heptane layer was concentrated under reduced pressure. The residue was dissolved in heptane (24.2 mL), followed by liquid-liquid extraction with acetonitrile (24.2 mL) twice. The heptane layer was concentrated under reduced pressure to obtain TIPS2-NH(CH$_2$)$_2$CH$_3$(C$_{14}$) (0.30 g).

$^1$H-NMR (400 MHz, CDCl$_3$) δ 1.03-1.08 (m, 45H), 1.22-1.39 (m, 36H), 1.39-1.58 (m, 10H), 1.68-1.90 (m, 5H), 2.54 (t, 2H), 3.67 (t, 4H), 3.72 (s, 2H), 3.87-3.96 (m, 4H), 6.39 (dd, 1H), 6.43 (d, 1H), 7.10 (d, 1H)

$^{13}$C-NMR (100 MHz, CDCl$_3$) δ 12.0, 12.2 (6C), 18.2 (12C), 23.3, 26.0 (2C), 26.2, 26.4, 29.5-29.8 (18C), 33.2 (2C), 49.3, 51.1, 63.7 (2C), 67.9, 68.2, 99.8, 104.3, 121.0, 130.5, 158.3, 159.6

ESIMS MH+ 918.8

Example 10

Synthesis of TIPS2-OH(C$_8$—O—C$_2$)

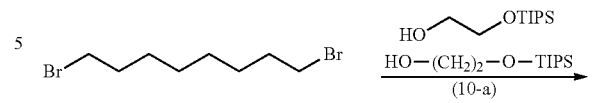

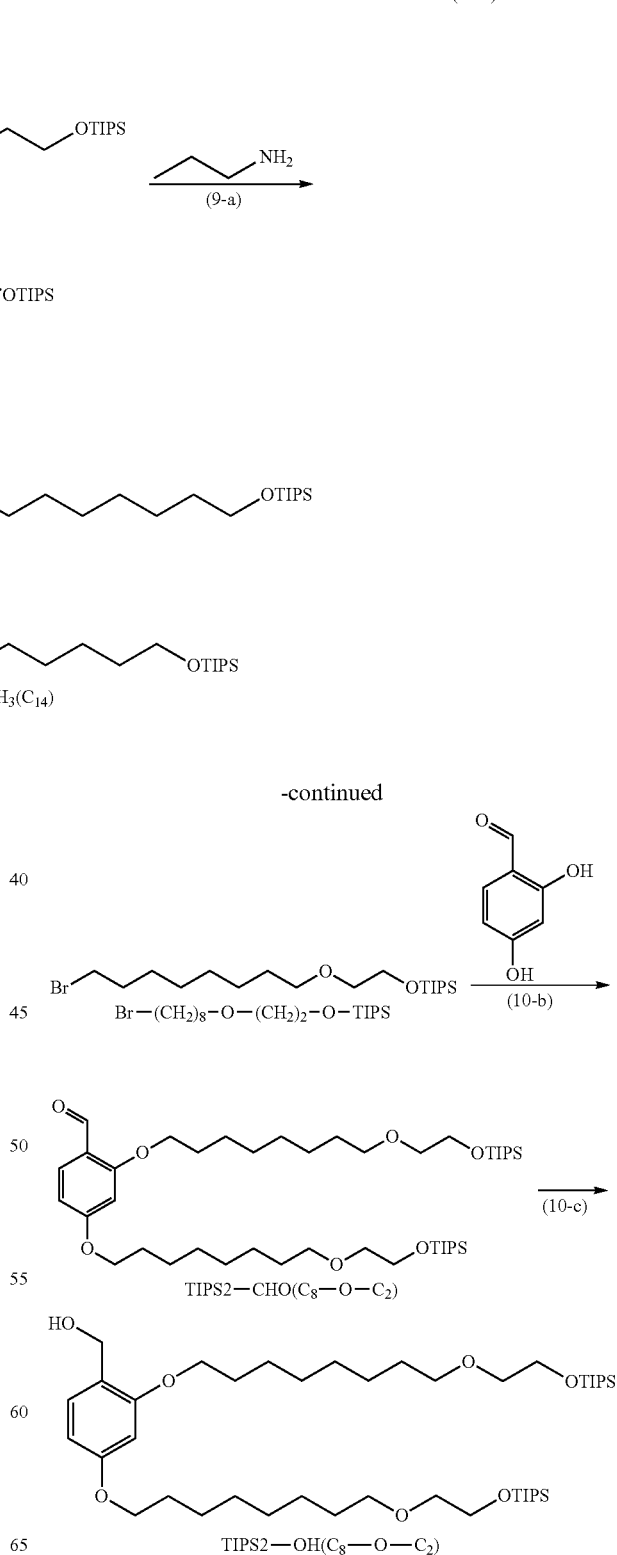

(Hereinafter, HO—(CH$_2$)$_2$—O-TIPS, Br—(CH$_2$)$_8$—O—(CH$_2$)$_2$—O-TIPS, TIPS2-CHO(C$_8$—O—C$_2$), and TIPS2-OH(C$_8$—O—C$_2$) indicate the respective structures in the formula.)

Example (10-a)

1,8-Dibromooctane (5.09 mL, 27.5 mmol) and HO—(CH$_2$)$_2$-OTIPS (3.00 g, 13.7 mmol) were dissolved in toluene (18 mL), and sodium hydride (60%, dispersed in liquid paraffin, 1.10 g, 27.5 mmol) was added thereto. The mixture was heated to 80° C. and was stirred for 20 hours. The reaction solution was cooled to 5° C., and the reaction was quenched with 1 N hydrochloric acid (27.5 mL). Toluene (18 mL) was added thereto, and the organic layer was separated from the mixture, followed by liquid-liquid extraction with 1 N hydrochloric acid (27 mL) once, a mixed solution of 5% sodium bicarbonate aqueous solution (27 mL) and 1 N hydrochloric acid (14 mL) once, and water (27 mL) once. Anhydrous sodium sulfate was added to the organic layer, and the mixture was thoroughly stirred and was then filtered. The filtrate was concentrated under reduced pressure. The resulting residue was purified by silica gel column chromatography (hexane:ethyl acetate=100:0→1:1) to obtain Br—(CH$_2$)$_8$—O—(CH$_2$)$_2$—O-TIPS (5.12 g).

ESIMS MH+ 409.0

Example (10-b): TIPS2-CHO(C$_8$—O—C$_2$)

TIPS2-CHO(C$_8$—O—C$_2$) was obtained by the same method as that for TIPS2-CHO(C$_{14}$) described above.

$^1$H-NMR (400 MHz, CDCl$_3$) δ 1.04-1.08 (m, 42H), 1.31-1.41 (m, 12H), 1.41-1.52 (m, 4H), 1.52-1.61 (m, 4H), 1.74-1.89 (m, 4H), 3.47 (t, 4H), 3.52 (t, 4H), 3.82 (t, 4H), 3.97-4.06 (m, 4H), 6.41 (d, 1H), 6.50 (dd, 1H), 7.79 (d, 1H), 10.32 (s, 1H)

ESIMS MH+ 795.6

Example (10-c): TIPS2-OH(C$_8$—O—C$_2$)

TIPS2-OH(C$_8$—O—C$_2$) was obtained by the same method as that for TIPS2-CHO(C$_{14}$) described above.

ESIMS MNa+ 819.6

Example 11

Synthesis of TIPS3-OH(C$_{10}$—CONH—C$_2$)

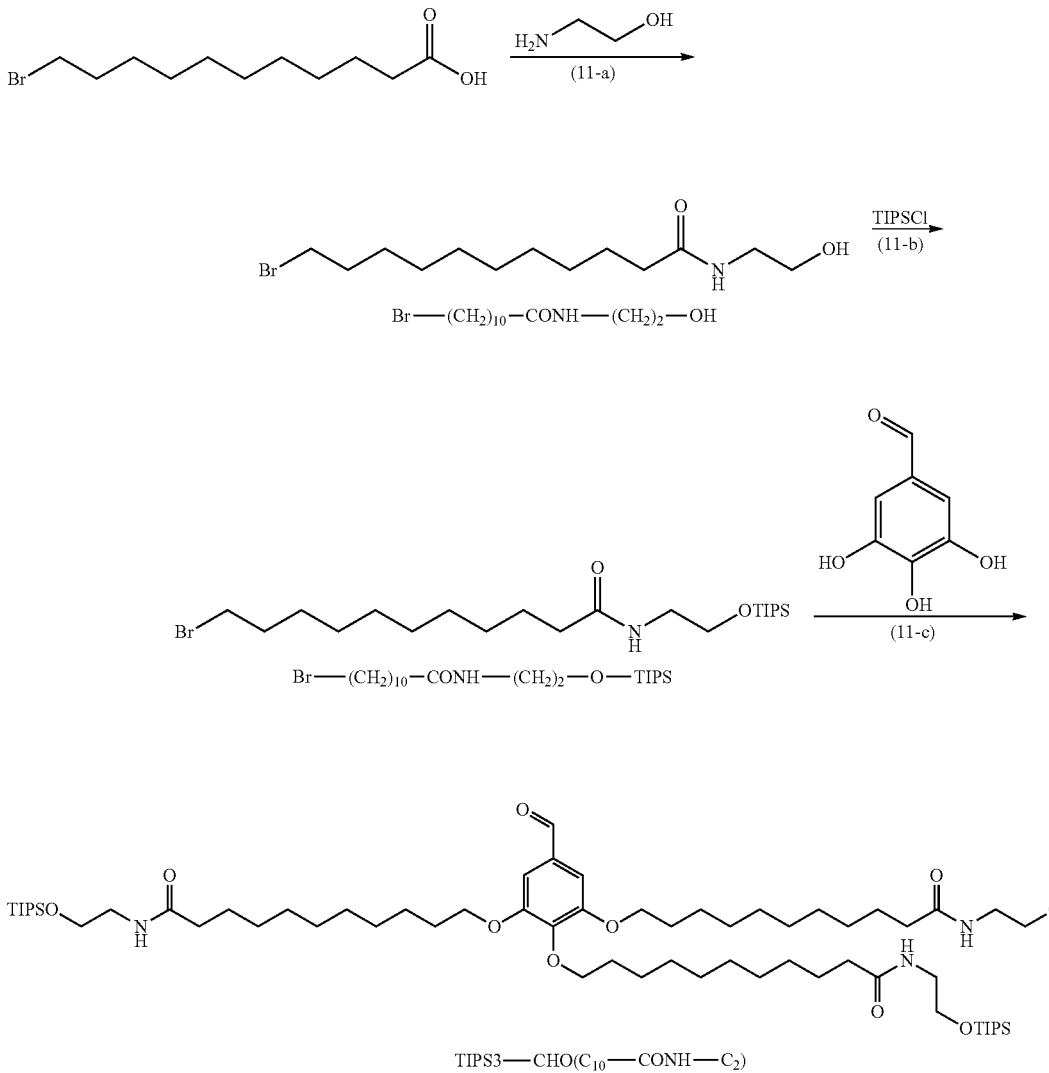

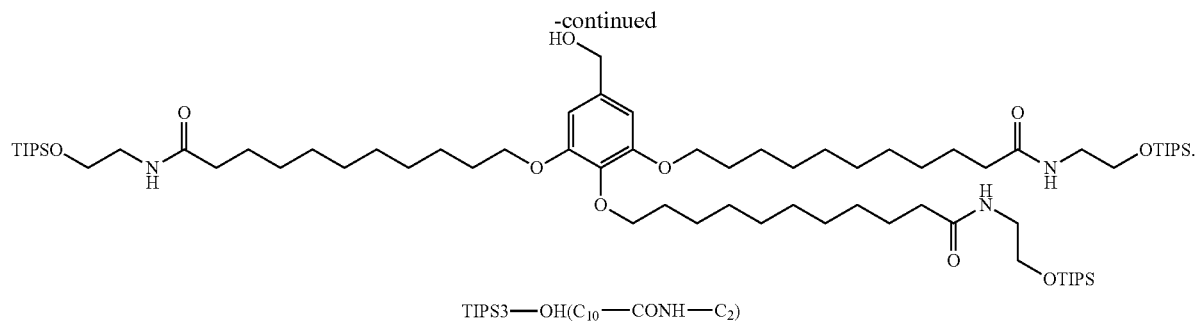

TIPS3—OH(C$_{10}$—CONH—C$_2$)

(Hereinafter, Br—(CH$_2$)$_{10}$—CONH—(CH$_2$)$_2$—OH, Br—(CH$_2$)$_{10}$—CONH—(CH$_2$)$_2$—O-TIPS, TIPS3-CHO(C$_{10}$—CONH—C$_2$), and TIPS3-OH(C$_{10}$—CONH—C$_2$) indicate the respective structures in the formula.)

Example (11-a)

11-Bromoundecanoic acid (8.00 g, 30.2 mmol) and ethanolamine (2.76 g, 45.3 mmol) were suspended in DMF (201 mL), and DMT-MM.1.8H$_2$O (18.65 g, 60.3 mmol) and DIPEA (21.0 mL, 120.7 mmol) were added thereto. The mixture was stirred at room temperature for 0.5 hours. Ethyl acetate (1,006 mL) was added to the reaction solution, followed by washing with a 5% sodium bicarbonate aqueous solution (503 mL) once and 20% sodium chloride aqueous solution (503 mL) three times. Anhydrous magnesium sulfate was added to the organic layer, and the mixture was thoroughly stirred and was then filtered. The filtrate was concentrated under reduced pressure. Hexane (93 mL) was added to the resulting residue, and the precipitate was collected by filtration and was dried under reduced pressure to obtain a mixture containing Br—(CH$_2$)$_{10}$—CONH—(CH$_2$)$_2$—OH.

Example (11-b)

The mixture obtained in the step (a) was dissolved in DMF (215 mL). Imidazole (4.52 g, 66.4 mmol) was added to the solution, and TIPSCl (7.0 mL, 33.2 mmol) was dropwise added to the mixture at room temperature. The mixture was then heated to 85° C. and was stirred for 1 hour and 10 minutes. TIPSCl (0.64 mL, 3.02 mmol) was further added to the mixture, followed by stirring at 85° C. for 20 minutes. Ethyl acetate (1,077 mL) was added to the reaction solution, and the mixture was washed with 1 N hydrochloric acid (539 mL) once, a 5% sodium bicarbonate aqueous solution (539 mL) once, and 20% sodium chloride aqueous solution (539 mL) twice. Anhydrous magnesium sulfate was added to the organic layer, and the mixture was thoroughly stirred and was then filtered. The filtrate was concentrated under reduced pressure to obtain Br—(CH$_2$)$_{10}$—CONH—(CH$_2$)$_2$—O-TIPS (13.8 g).

$^1$H-NMR (400 MHz, CDCl$_3$) δ 1.02-1.05 (m, 21H), 1.24-1.33 (m, 10H), 1.39 (quin., 2H), 1.60 (quin., 2H), 1.74 (quin., 2H), 2.15 (t, 2H), 3.37 (q, 2H), 3.50 (t, 2H), 3.73 (t, 2H), 5.90 (t, 1H)

Example (11-c): TIPS3-CHO(C$_{10}$—CONH—C$_2$)

Br—(CH$_2$)$_{10}$—CONH—(CH$_2$)$_2$—O-TIPS (1.44 g, 3.09 mmol), 3,4,5-trihydroxybenzaldehyde (0.12 g, 0.77 mmol), and potassium carbonate (0.64 g, 4.64 mmol) were suspended in DMF (5.2 mL), and the suspension was heated to 115° C. and was stirred for 4 hours. The reaction solution was filtered, and ethyl acetate (51.5 mL) was added to the filtrate, followed by liquid-liquid extraction with water (46.4 mL) four times. Anhydrous sodium sulfate was added to the organic layer, and the mixture was thoroughly stirred and was then filtered. The filtrate was concentrated under reduced pressure to obtain TIPS3-CHO(C$_{10}$—CONH—C$_2$) (1.16 g).

ESIMS MH+ 1,304.9

Example (11-d): TIPS3-OH(C$_{10}$—CONH—C$_2$)

TIPS3-CHO(C$_{10}$—CONH—C$_2$) (0.66 g, 0.51 mmol) was dissolved in a mixed solution of THF (anhydrous, 3.85 mL) and methanol (0.19 mL), and sodium borohydride (23 mg, 0.61 mmol) was added to the solution, followed by stirring at room temperature for 1 hour. The reaction solution was cooled to 5° C., and 1 N hydrochloric acid (0.48 mL) was added thereto to quench the reaction. CPME (16.5 mL) was added to the solution, followed by liquid-liquid extraction with 1 N hydrochloric acid (4.9 mL) twice, a 5% sodium bicarbonate aqueous solution (4.9 mL) once, and water (4.9 mL) once. Anhydrous sodium sulfate was added to the organic layer, and the mixture was thoroughly stirred and was then filtered. The filtrate was concentrated under reduced pressure to obtain TIPS3-OH(C$_{10}$—CONH—C$_2$) (0.64 g).

ESIMS MNa+ 1,329.0

Example 12

Synthesis of TIPS6-OH(C$_{10}$—CONH—CH(CH$_2$)$_2$)

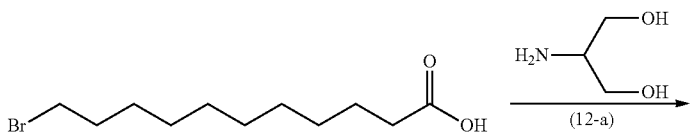

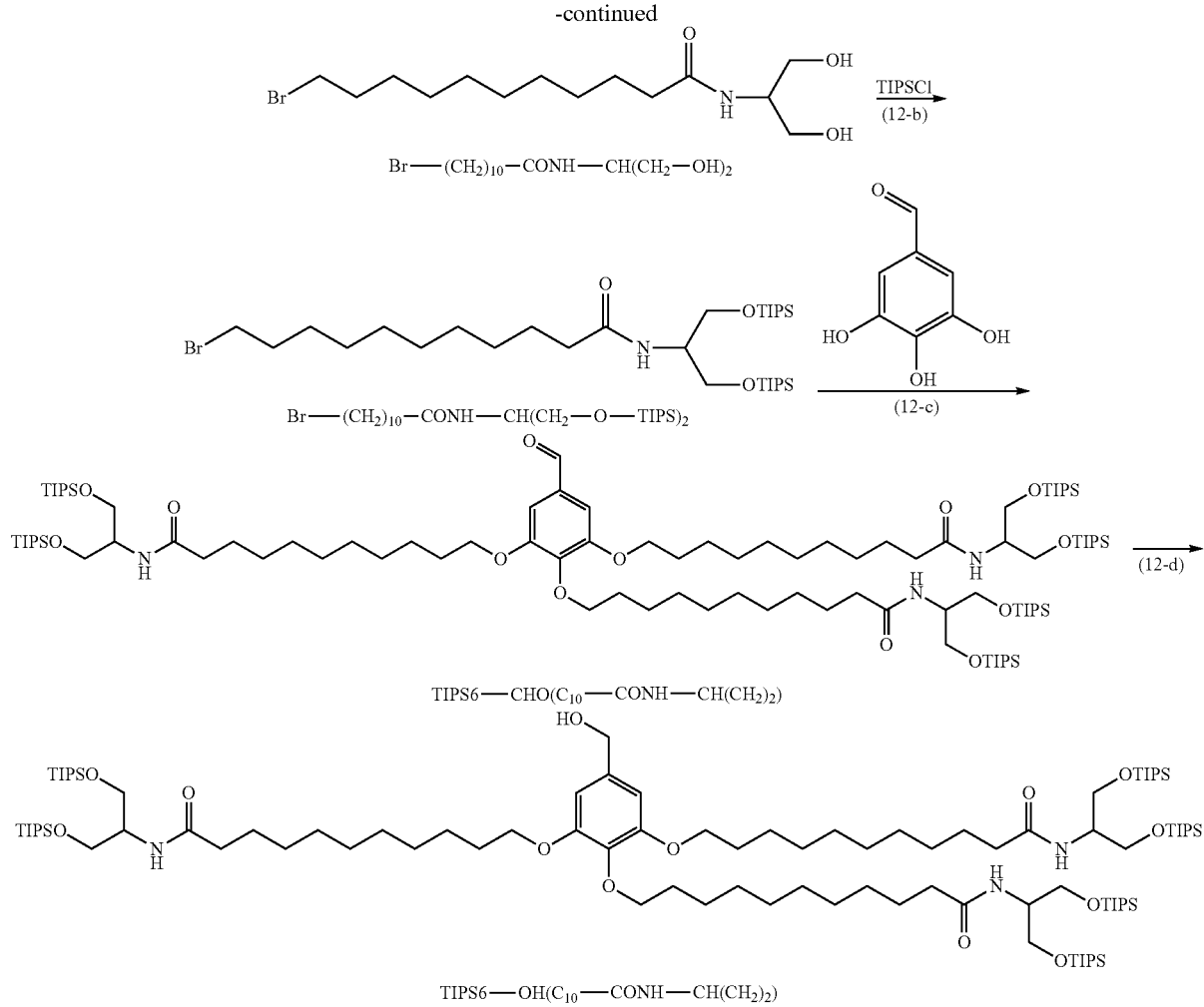

(Hereinafter, Br—(CH$_2$)$_{10}$—CONH—CH(CH$_2$—OH)$_2$, Br—(CH$_2$)$_{10}$—CONH—CH(CH$_2$—O-TIPS)$_2$, TIPS6-CHO (C$_{10}$—CONH—CH(CH$_2$)$_2$), and TIPS6-OH(C$_{10}$—CONH—CH(CH$_2$)$_2$) indicate the respective structures in the formula.)

Examples (12-a) and (12-b)

A mixture containing Br—(CH$_2$)$_{10}$—CONH—CH(CH$_2$—OH)$_2$ was (CH$_2$)$_2$—OH described above. This mixture (10.2 g) containing Br—(CH$_2$)$_{10}$—CONH—CH(CH$_2$—OH)$_2$ was dissolved in DMF (215 mL), and imidazole (9.04 g, 132.7 mmol) was added thereto. TIPSCl (14.1 mL, 66.4 mmol) was dropwise added to the mixture at room temperature. The mixture was then heated to 85° C. and was stirred for 2 hours and 10 minutes. Ethyl acetate (1,077 mL) was added to the reaction solution, followed by washing with 1 N hydrochloric acid (539 mL) once, a 5% sodium bicarbonate aqueous solution (539 mL) once, and 20% sodium chloride aqueous solution (539 mL) twice. Anhydrous magnesium sulfate was added to the organic layer, and the mixture was thoroughly stirred and was then filtered. The filtrate was concentrated under reduced pressure to obtain Br—(CH$_2$)$_{10}$—CONH—CH(CH$_2$—O-TIPS)$_2$ (19.7 g).

$^1$H-NMR (400 MHz, CDCl$_3$) δ 1.03-1.07 (m, 42H), 1.24-1.34 (m, 10H), 1.40 (quin., 2H), 1.59 (quin., 2H), 1.75 (quin., 2H), 2.14 (t, 2H), 3.51 (t, 2H), 3.63-3.70 (m, 2H), 3.85-3.90 (m, 2H), 3.93-4.03 (m, 1H), 5.83 (d, 1H)

Example (12-c): TIPS6-CHO(C$_{10}$—CONH—CH(CH$_2$)$_2$)

Br—(CH$_2$)$_{10}$—CONH—CH(CH$_2$—O-TIPS)$_2$ (2.02 g, 3.10 mmol), 3,4,5-trihydroxybenzaldehyde (0.13 g, 0.86 mmol), and potassium carbonate (0.61 g, 4.39 mmol) were suspended in DMF (5.7 mL), and the suspension was heated to 115° C. and was stirred for 9 hours. Br—(CH$_2$)$_{10}$—CONH—CH(CH$_2$—O-TIPS)$_2$ (0.22 g, 0.34 mmol) was further added thereto, and the mixture was stirred at 115° C. for 1 hour. The reaction solution was filtered, and the residue was washed with heptane (12.0 mL). The heptane layer was separated from the filtrate, and heptane (5.7 mL) was added to the layer, followed by liquid-liquid extraction with DMF (5.7 mL). Heptane (5.7 mL) was added to the resulting heptane layer, followed by liquid-liquid extraction with 1 N hydrochloric acid (5.7 mL) once, a 5% sodium bicarbonate aqueous solution (5.7 mL) once, and water (5.7 mL) once. Heptane (5.7 mL) was added to the resulting heptane layer, followed by liquid-liquid extraction with acetonitrile (5.7 mL). The liquid-liquid extraction with heptane and acetonitrile was further repeated once, and the heptane layer was concentrated under reduced pressure to obtain TIPS6-CHO (C$_{10}$—CONH—CH(CH$_2$)$_2$) (1.05 g).

¹H-NMR (400 MHz, CDCl₃) δ 1.03-1.08 (m, 126H), 1.23-1.39 (m, 30H), 1.39-1.51 (m, 6H), 1.55-1.67 (m, 6H), 1.70-1.87 (m, 6H), 2.15 (t, 6H), 3.63-3.70 (m, 6H), 3.86-3.91 (m, 6H), 3.95-4.07 (m, 9H), 5.84 (d, 3H), 7.07 (s, 2H), 9.82 (s, 1H)

ESIMS MH+ 1,864.0

Example (12-d): TIPS6-OH(C₁₀—CONH—CH(CH₂)₂)

TIPS6-OH(C₁₀—CONH—CH(CH₂)₂) was obtained by the same method as that for TIPS3-OH(C₁₀—CONH—C₂).

ESIMS MH+ 1,865.5

Example 13

Synthesis of TIPS3-OH(4-OMe)

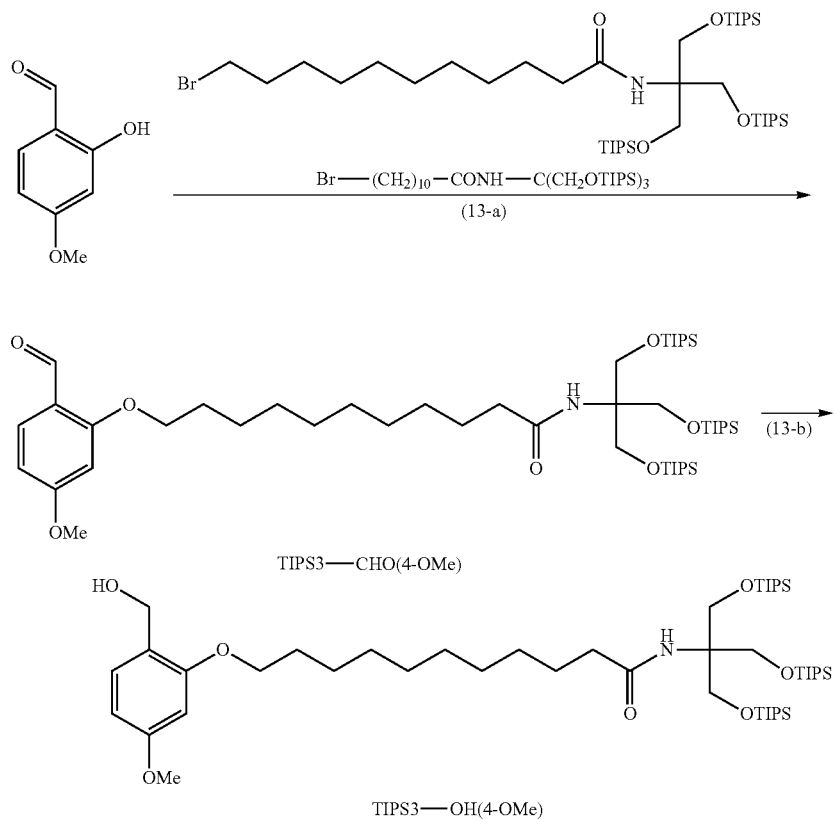

(Hereinafter, TIPS3-CHO(4-OMe) and TIPS3-OH(4-OMe) indicate the respective structures in the formula.)

Example (13-a): TIPS3-CHO(4-OMe)

Br—(CH₂)₁₀—CONH—C(CH₂OTIPS)₃ (3.13 g, 3.74 mmol), 2-hydroxy-4-methoxybenzaldehyde (0.68 g, 4.49 mmol), and potassium carbonate (1.24 g, 8.98 mmol) were suspended in DMF (24.9 mL), and the suspension was heated to 120° C. and was stirred for 3.5 hours. The reaction solution was filtered, and the residue was washed with heptane (34.0 mL). The heptane layer was separated from the filtrate, and heptane (17.0 mL) was added to the layer, followed by liquid-liquid extraction with DMF (17.0 mL). The liquid-liquid extraction with heptane and DMF was further repeated once. Heptane (17.0 mL) was added to the resulting heptane layer, followed by liquid-liquid extraction with 1 N hydrochloric acid (17.0 mL) once, a 5% sodium bicarbonate aqueous solution (17.0 mL) once, and water (17.0 mL) once. The heptane layer was concentrated under reduced pressure, and the resulting residue was dissolved in heptane (17.0 mL), followed by liquid-liquid extraction with acetonitrile (17.0 mL). The liquid-liquid extraction with heptane and acetonitrile was further repeated once, and the heptane layer was concentrated under reduced pressure to obtain TIPS3-CHO(4-OMe) (1.64 g).

¹H-NMR (400 MHz, CDCl₃) δ 1.03-1.10 (m, 63H), 1.24-1.39 (m, 10H), 1.48 (quin., 2H), 1.56 (quin., 2H), 1.83 (quin., 2H), 2.08 (t, 2H), 3.86 (s, 3H), 4.00-4.06 (m, 8H), 5.75 (s, 1H), 6.42 (d, 1H), 6.52 (dd, 1H), 7.81 (d, 1H), 10.33 (s, 1H)

ESIMS MH+ 908.7

Example (13-b): TIPS3-OH(4-OMe)

TIPS3-OH(4-OMe) was obtained by the same method as that for TIPS2-OH(C₈).

¹H-NMR (400 MHz, CDCl₃) δ 1.03-1.10 (m, 63H), 1.24-1.39 (m, 10H), 1.45 (quin., 2H), 1.57 (quin., 2H), 1.80 (quin., 2H), 2.08 (t, 2H), 2.31 (br, 1H), 3.79 (s, 3H), 3.98 (t, 2H), 4.04 (s, 6H), 4.61 (s, 2H), 5.75 (s, 1H), 6.41-6.47 (m, 2H), 7.16 (d, 1H)

¹³C-NMR (100 MHz, CDCl₃) δ 12.1 (9C), 18.1 (18C), 25.9, 26.3, 29.4-29.7 (6C), 37.9, 55.5, 61.3 (3C), 62.0, 62.2, 68.1, 99.4, 103.9, 122.1, 129.6, 158.2, 160.7, 172.6

ESIMS MNa+ 932.7

Example 14

Validation of Performance of Enhancing Solubility of Peptide Compound

Peptide used as model: H-Gly-Gly-Gly-OH

H-Gly-Gly-Gly-OH (model peptide), H-Gly-Gly-Gly-O-TIPS2, H-Gly-Gly-Gly-O-TIPS3, and H-Gly-Gly-Gly-O-TIPS6 were synthesized, and the solubility at 25° C. of each peptide in cyclopentyl methyl ether (CPME) was measured. As a result, merely 0.032 mM of H-Gly-Gly-Gly-OH was dissolved in CPME when a TIPS-type protecting agent was not combined to the peptide. However, 181 mM and 175 mM of the peptide were dissolved when TIPS2-OH and TIPS3-OH were combined to the peptide, and 286 mM of the peptide was dissolved when TIPS6-OH was combined to the peptide. The solubility was thus enhanced by about 5,000-fold and about 9,000-fold, respectively. The results are shown in FIG. 1.

The results demonstrated that the solubility of the peptide used as a model was significantly enhanced by derivatizing the peptide with a novel benzyl-type compound. H-Gly-Gly-Gly-O-TIPS2, H-Gly-Gly-Gly-O-TIPS3, and H-Gly-Gly-Gly-O-TIPS6 indicate the following structures.

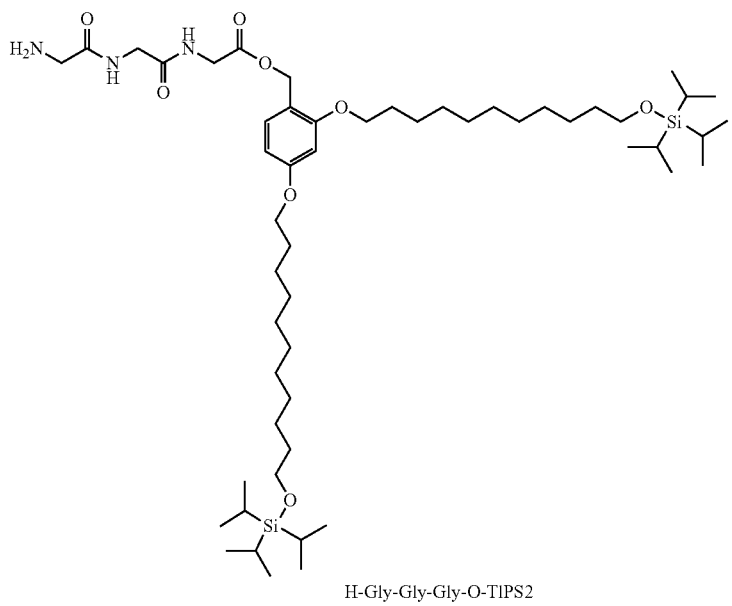

H-Gly-Gly-Gly-O-TIPS2

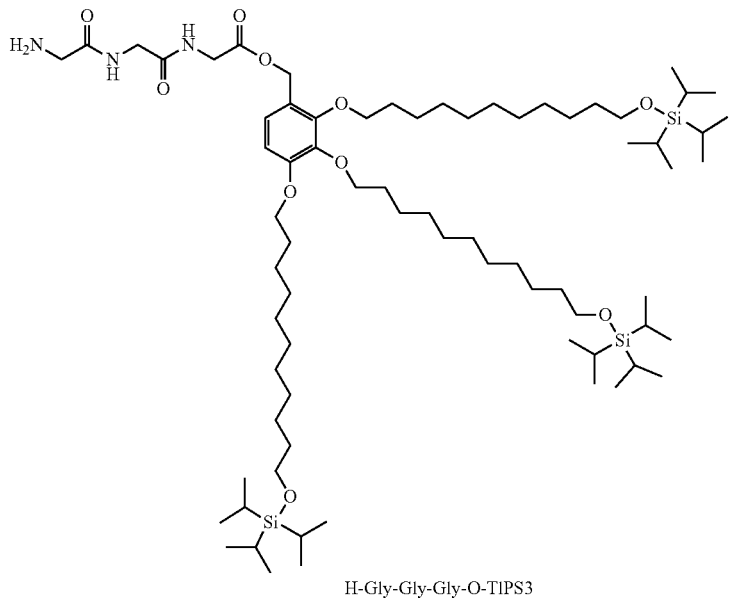

H-Gly-Gly-Gly-O-TIPS3

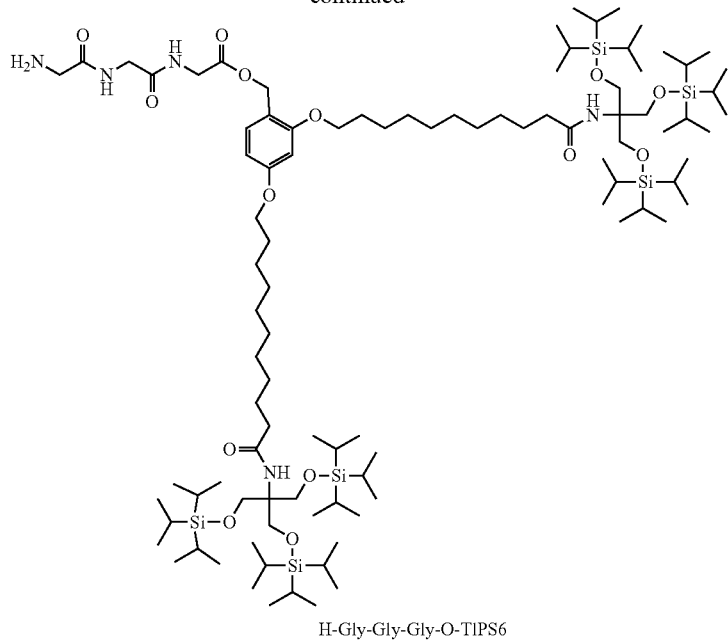

H-Gly-Gly-Gly-O-TIPS6

Example (14-a)

Synthesis of H-Gly-Gly-Gly-O-TIPS2

TIPS2-OH (0.81 g, 1.02 mmol) was dissolved in CPME (16.2 mL). DMF (4.1 mL), Fmoc-Gly-OH (0.91 g, 3.05 mmol), WSCI.HCl (0.58 g, 3.05 mmol), and DMAP (12.4 mg, 0.10 mmol) were added to the solution, followed by stirring at room temperature for 2 hours. After confirmation of disappearance of TIPS2-OH, DBU (1.76 mL, 11.8 mmol) was added to the mixture, followed by stirring at room temperature for 10 minutes. The reaction solution was cooled to 5° C., and 4 M CPME/HCl (3.54 mL) was then dropwise added thereto. The mixture was warmed to room temperature, and CPME (0.81 mL), 20% sodium chloride aqueous solution (21 mL), and a 10% sodium carbonate aqueous solution (18 mL) were added thereto for liquid-liquid extraction. 20% sodium chloride aqueous solution (38 mL), DMSO (1.0 mL), and DMF (1.0 mL) were added to the resulting organic phase for liquid-liquid extraction. A 50% dipotassium hydrogen phosphate aqueous solution (19 mL), DMSO (0.5 mL), and DMF (0.5 mL) were added to the resulting organic phase for liquid-liquid extraction. A 50% dipotassium hydrogen phosphate aqueous solution (19 mL), DMSO (0.5 mL), and DMF (0.5 mL) were added to the resulting organic phase for liquid-liquid extraction to obtain a mixed liquid containing H-Gly-O-TIPS2. H-Gly-O-TIPS2 indicates the following structure.

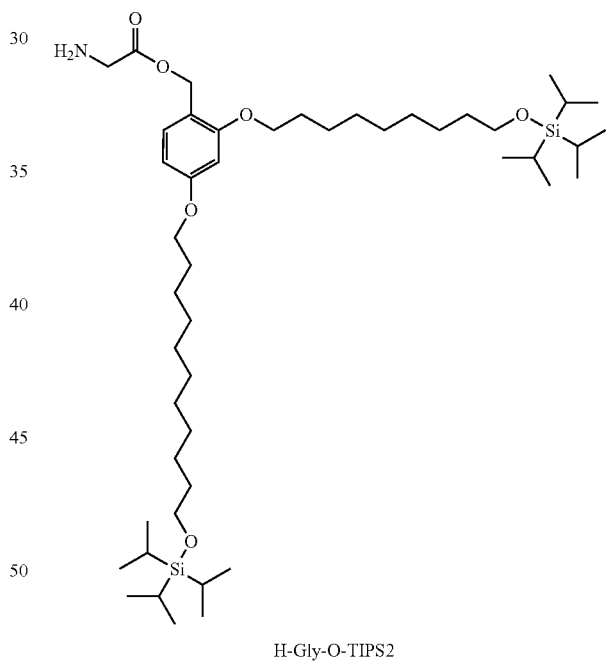

H-Gly-O-TIPS2

CPME (1.4 mL), DMF (5.1 mL), Fmoc-Gly-Gly-OH (1.08 g, 3.05 mmol), WSCI.HCl (0.58 g, 3.05 mmol), and DIPEA (0.71 mL, 4.06 mmol) were added to the resulting mixed liquid, and the mixture was stirred at room temperature for 1.5 hours. After confirmation of disappearance of H-Gly-O-TIPS2, DBU (1.76 mL, 11.8 mmol) was added to the mixture, followed by stirring at room temperature for 10 minutes. The reaction solution was cooled to 5° C., and 4 M CPME/HCl (3.50 mL) was then dropwise added thereto. The mixture was warmed to room temperature, and CPME (0.86 mL), 20% sodium chloride aqueous solution (24 mL), and a 10% sodium carbonate aqueous solution (20 mL) were added thereto for liquid-liquid extraction. A 20% sodium chloride aqueous solution (44 mL), DMSO (1.2 mL), DMF (1.2 mL), and a 50% dipotassium hydrogen phosphate aqueous solution (15 mL) were added to the resulting organic phase for liquid-liquid extraction. A 50% dipotassium hydrogen phosphate aqueous solution (22 mL), DMSO (0.6 mL), and DMF (0.6 mL) were added to the resulting organic phase for liquid-liquid extraction. A 50% dipotassium hydrogen phosphate aqueous solution (22 mL), DMSO (0.6 mL), and DMF (0.6 mL) were added to the resulting organic phase for liquid-liquid extraction. The resulting organic phase was concentrated under reduced pressure to distill the solvent. Acetonitrile (28 mL) was added to the resulting residue, and precipitate was collected by filtration. Acetonitrile (28 mL) was added to the collected precipitate to wash the precipitate, and the precipitate was collected by filtration. The precipitate was further washed with acetonitrile twice and was dried under reduced pressure to obtain H-Gly-Gly-Gly-O-TIPS2 (0.95 g, 97.3%).

ESIMS MH+ 964.8

H-Gly-Gly-Gly-O-TIPS3 (yield: 88.7%, ESIMS MH+1, 307.2) and H-Gly-Gly-Gly-O-TIPS6 (yield: 69.4%, ESIMS MH+ 1,823.3) were synthesized by the same method as that for H-Gly-Gly-Gly-O-TIPS2.

Example (14-b): Synthesis of H-Gly-Gly-Gly-OH

A mixed solution of trifluoroacetic acid (1.04 mL, 13.6 mmol), 3,6-dioxa-1,8-octanedithiol (27 μL, 0.168 mmol), and triisopropylsilane (27 μL, 0.127 mmol) was cooled to 5° C., and H-Gly-Gly-Gly-O-TIPS2 (53 mg, 0.055 mmol) was added thereto. The mixture was warmed to room temperature and was stirred for 1 hour. After confirmation of disappearance of H-Gly-Gly-Gly-O-TIPS2, the reaction solution was concentrated under reduced pressure. Diisopropyl ether (3.5 mL) was added to the residue. The mixture was cooled to 5° C., and the precipitate was collected by filtration. The washing of the precipitate with diisopropyl ether and filtration were further repeated three times, and the precipitate was collected by filtration. The precipitate was dried under reduced pressure to obtain H-Gly-Gly-Gly-OH (9.8 mg).

ESIMS MH+ 189.9

The invention claimed is:

1. A benzyl compound of formula (1):

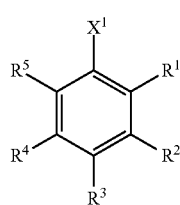

(1)

wherein $X^1$ represents —$CH_2OR^{14}$ where $R^{14}$ represents a hydrogen atom, a halogenocarbonyl group, or an active ester-type protecting group, —$CH_2NHR^{15}$ where $R^{15}$ represents a hydrogen atom, a linear or branched alkyl group having 1 to 6 carbon atoms, or an aralkyl group, a halogenomethyl group, a methyl azide group, a formyl group, or an oxime; and at least one of $R^1$, $R^2$, $R^3$, $R^4$, and $R^5$ is a group of formula (2):

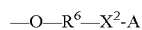

(2)

and the remainders each represent a hydrogen atom, a halogen atom, an alkyl group having 1 to 4 carbon atoms, or an alkoxy group having 1 to 4 carbon atoms, wherein $R^6$ represents a linear or branched alkylene group having 1 to 16 carbon atoms;

$X^2$ represents O or $CONR^{16}$ where $R^{16}$ represents a hydrogen atom or an alkyl group having 1 to 4 carbon atoms; and A is a group of formula (3), (4), (5), (6), (7), (8), (9), (10), (11), (12), or (13):

(3)

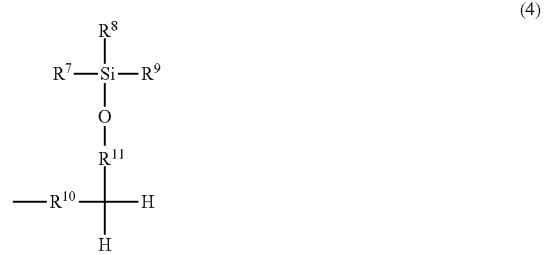

(4)

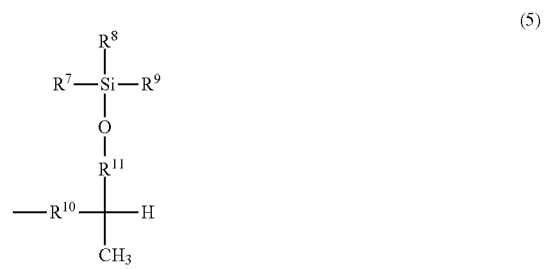

(5)

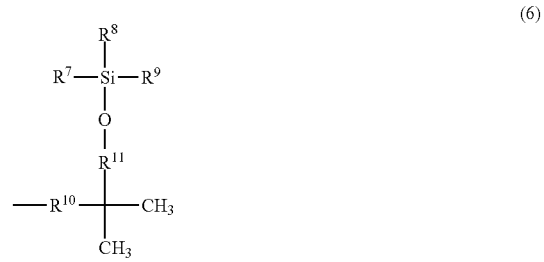

(6)

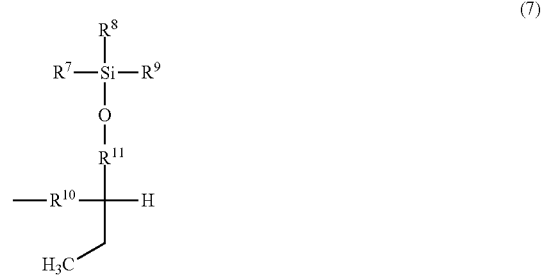

(7)

(8) 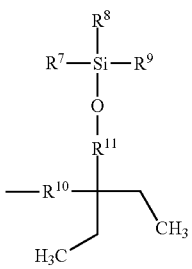

(9) 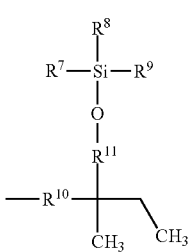

(10) 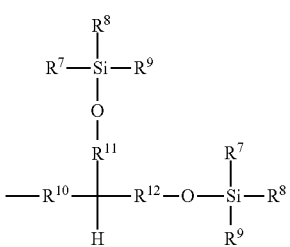

(11) 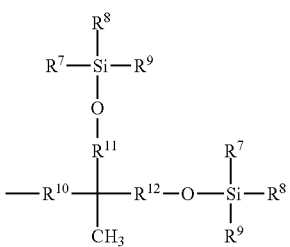

(12) 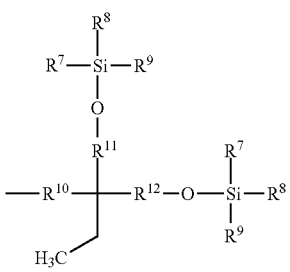

(13) 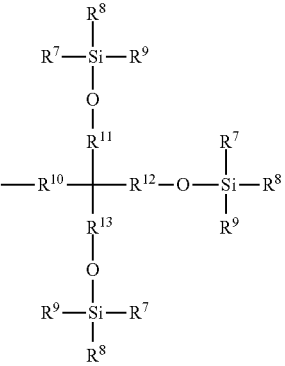

wherein $R^7$, $R^8$, and $R^9$ are the same or different and each represent a linear or branched alkyl group having 1 to 6 carbon atoms or an optionally substituted aryl group; $R^{10}$ represents a single bond or a linear or branched alkylene group having 1 to 3 carbon atoms; and $R^{11}$, $R^{12}$, and $R^{13}$ each represent a linear or branched alkylene group having 1 to 3 carbon atoms, wherein when A is a group of formula (3), $R^7$, $R^8$, and $R^9$ are the same.

2. The benzyl compound according to claim 1, wherein $X^1$ is —$CH_2OR^{14}$ where $R^{14}$ represents a hydrogen atom, a halogenocarbonyl group, or an active ester-type protecting group, —$CH_2NHR^{15}$ where $R^{15}$ represents a hydrogen atom, a linear or branched alkyl group having 1 to 6 carbon atoms, or an aralkyl group, or a halogenomethyl group.

3. The benzyl compound according to claim 1, wherein $R^6$ is a linear or branched alkylene group having 2 to 16 carbon atoms.

4. The benzyl compound according to claim 1, wherein $R^6$ is a linear or branched alkylene group having 6 to 16 carbon atoms.

5. The benzyl compound according to claim 1, wherein:
A is a group of formula (4), (5), (6), (7), (8), (9), (10), (11), (12), or (13);
$R^{10}$ is a single bond or a methylene group; and
$R^{11}$, $R^{12}$ and $R^{13}$ are methylene groups.

6. A method, comprising protecting a carboxy group, a hydroxy group, a diol group, an amino group, or a mercapto group, with the benzyl compound according to claim 1 as a protecting agent.

7. The benzyl compound according to claim 1, wherein $R^6$ represents a linear or branched alkylene group having from 4 to 16 carbon atoms.

8. The benzyl compound according to claim 1, wherein $X^1$ is $CH_2OH$, $R^1$ and $R^3$ are each O—$(CH_2)_{11}$—O-TIPS, and $R^2$, $R^4$ and $R^5$ are each hydrogen.

9. A benzyl compound of formula (1):

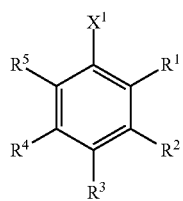

(1)

wherein:
$X^1$ represents $CH_2OH$;
$R^1$ and $R^3$ are each a group of formula (2):
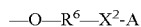 (2)
—O—$R^6$—$X^2$-A
$R^2$, $R^4$ and $R^5$ are each hydrogen;
$R^6$ represents a linear or branched alkylene group having 1 to 16 carbon atoms;
$X^2$ represents $CONR^{16}$ where $R^{16}$ represents a hydrogen atom or an alkyl group having 1 to 4 carbon atoms; and
A is a group of formula (3), (4), (5), (6), (7), (8), (9), (10), (11), (12), or (13):
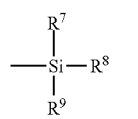 (3)
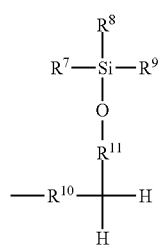 (4)
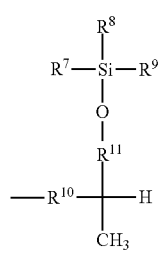 (5)
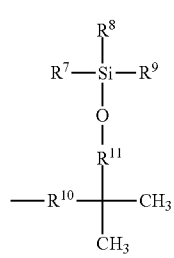 (6)
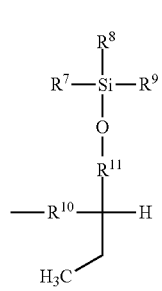 (7)
-continued
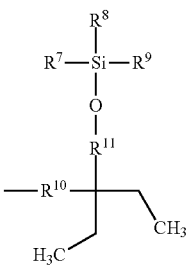 (8)
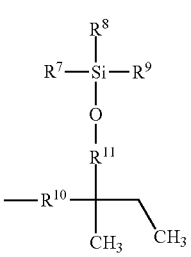 (9)
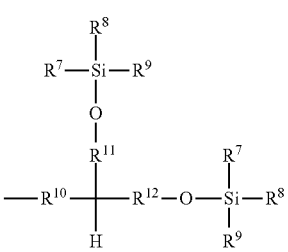 (10)
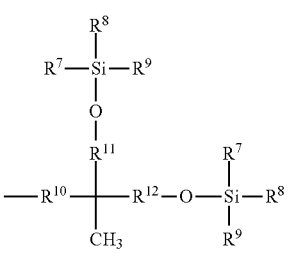 (11)
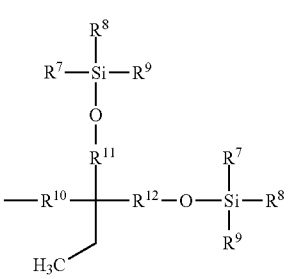 (12)

(13)

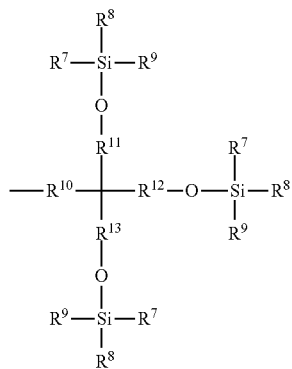

wherein $R^7$, $R^8$, and $R^9$ are the same or different and each represent a linear or branched alkyl group having 1 to 6 carbon atoms or an optionally substituted aryl group; $R^{10}$ represents a single bond or a linear or branched alkylene group having 1 to 3 carbon atoms; and $R^{11}$, $R^{12}$, and $R^{13}$ each represent a linear or branched alkylene group having 1 to 3 carbon atoms.

10. The benzyl compound according to claim 9, wherein A is a group of formula (13).

11. A benzyl compound of formula (1):

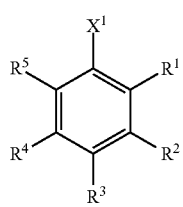
(1)

wherein:
$X^1$ represents $CH_2OH$;
$R^1$, $R^2$, and $R^3$ are each a group of formula (2):

$$-O-R^6-X^2-A \quad (2)$$

$R^4$ and $R^5$ are each hydrogen;
$R^6$ represents a linear or branched alkylene group having 1 to 16 carbon atoms;
$X^2$ represents $CONR^{16}$ where $R^{16}$ represents a hydrogen atom or an alkyl group having 1 to 4 carbon atoms; and
A is a group of formula (3), (4), (5), (6), (7), (8), (9), (10), (11), (12), or (13):

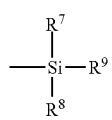
(3)

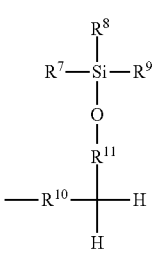
(4)

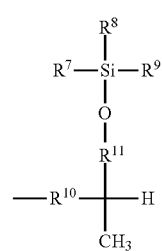
(5)

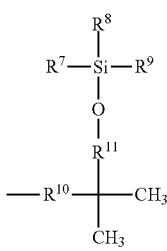
(6)

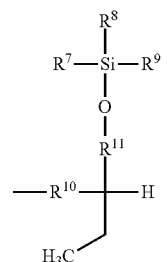
(7)

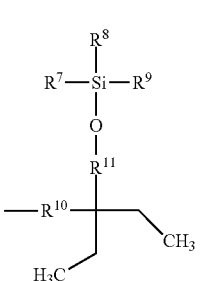
(8)

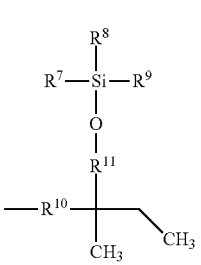
(9)

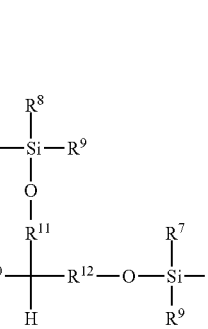
(10)

(11)

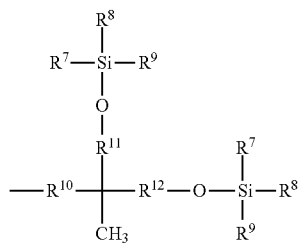

(12)

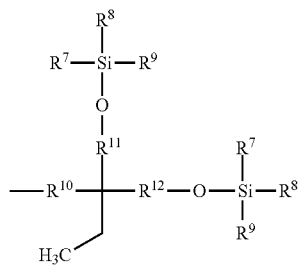

(13)

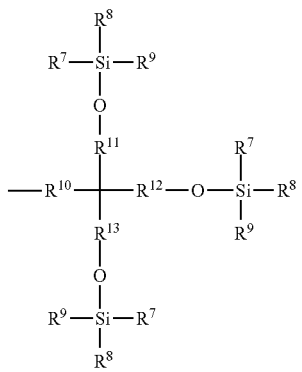

wherein $R^7$, $R^8$, and $R^9$ are the same or different and each represent a linear or branched alkyl group having 1 to 6 carbon atoms or an optionally substituted aryl group; $R^{10}$ represents a single bond or a linear or branched alkylene group having 1 to 3 carbon atoms; and $R^{11}$, $R^{12}$, and $R^{13}$ each represent a linear or branched alkylene group having 1 to 3 carbon atoms.

12. The benzyl compound according to claim 11, wherein A is a group of formula (13).

13. A benzyl compound, wherein the compound is selected from the group consisting of:

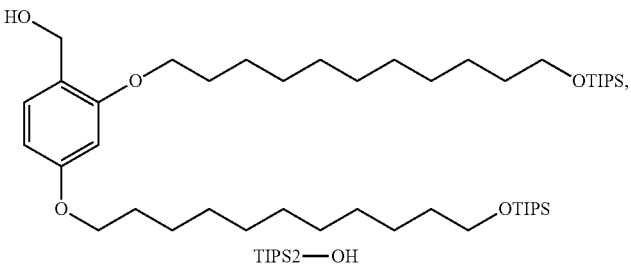

TIPS2—OH

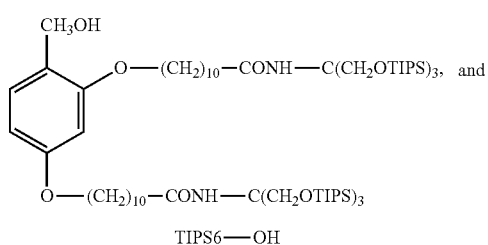

TIPS6—OH

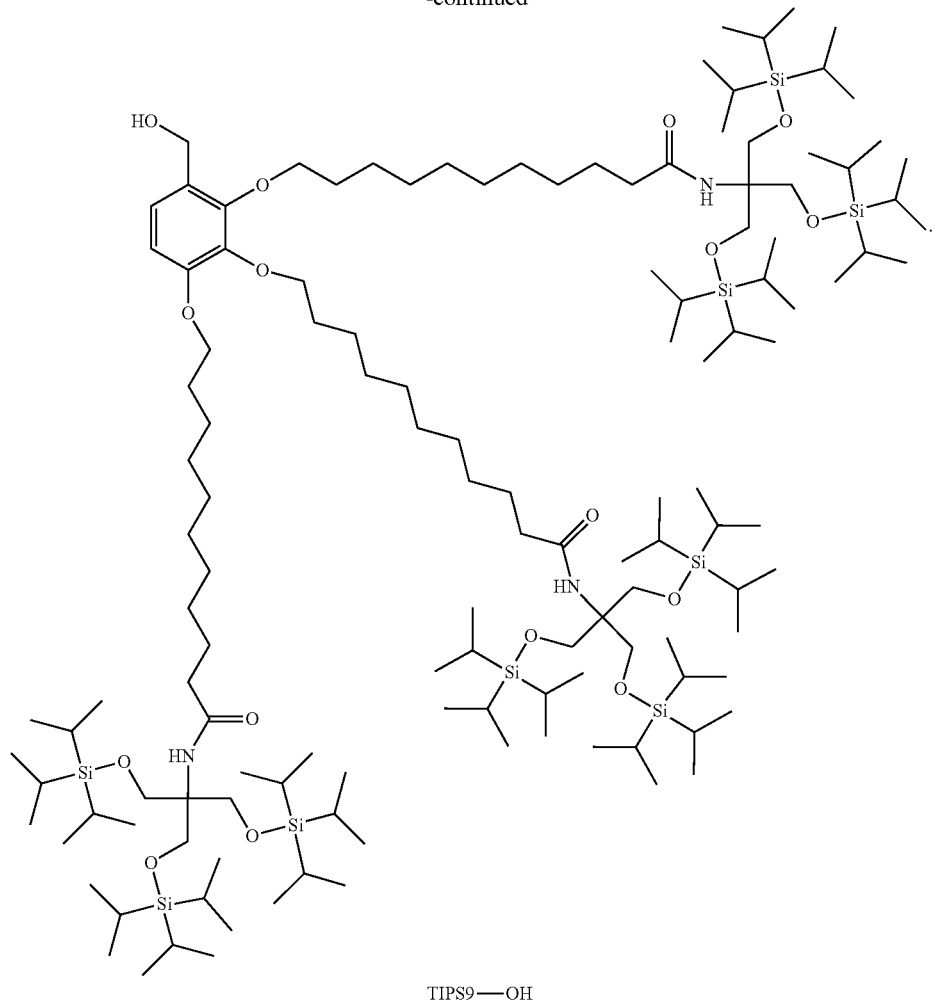
TIPS9—OH
* * * * *